much((12) United States Patent
Magro et al.

(10) Patent No.: US 8,859,213 B2
(45) Date of Patent: Oct. 14, 2014

(54) METHOD FOR DIAGNOSING MELANOCYTIC PROLIFERATIONS

(75) Inventors: Cynthia Magro, New York, NY (US); Jonathan Zippin, New York, NY (US); Lonny R. Levin, New York, NY (US); Jochen Buck, Greenwich, CT (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/642,475

(22) PCT Filed: Apr. 6, 2011

(86) PCT No.: PCT/US2011/031466
§ 371 (c)(1),
(2), (4) Date: Oct. 19, 2012

(87) PCT Pub. No.: WO2011/133327
PCT Pub. Date: Oct. 27, 2011

(65) Prior Publication Data
US 2013/0065246 A1     Mar. 14, 2013

Related U.S. Application Data

(60) Provisional application No. 61/326,174, filed on Apr. 20, 2010.

(51) Int. Cl.
*G01N 33/53* (2006.01)
*G01N 33/574* (2006.01)
*G01N 33/50* (2006.01)
*C12Q 1/527* (2006.01)
*G01N 33/68* (2006.01)

(52) U.S. Cl.
CPC ........ *G01N 33/5743* (2013.01); *G01N 33/5044* (2013.01); *G01N 33/5026* (2013.01); *C12Q 1/527* (2013.01); *G01N 33/6893* (2013.01); *G01N 2800/56* (2013.01); *G01N 2800/20* (2013.01); *G01N 33/5076* (2013.01)
USPC .......................................... 435/7.1; 435/7.23

(58) Field of Classification Search
None
See application file for complete search history.

(56) References Cited

U.S. PATENT DOCUMENTS

| 4,208,479 | A * | 6/1980 | Zuk et al. ........................ 435/7.9 |
| 6,544,768 | B1 * | 4/2003 | Buck et al. ..................... 435/232 |
| 2007/0244174 | A1 * | 10/2007 | Buck et al. ..................... 514/395 |

FOREIGN PATENT DOCUMENTS

| WO | WO 01/85753 | | 11/2001 |
| WO | WO 2009/111661 A1 | | 9/2009 |

OTHER PUBLICATIONS

Magro et al. (Lab. Investig. Feb. 2011 91(suppl. 1): 394A, Abstract 1678).*
Garbe et al. (Eur. J. Cancer, Dec. 2009, 46: 270-283).*
Acin-Perez R, Salazar E, Kamenetsky M, Buck J, Levin LR, Manfredi G. "Cyclic AMP produced inside mitochondria regulates oxidative phosphorylation", *Cell Metab.*, 9(3):265-276 (Mar. 2009).
Blokx et al., *Histopathol.*, 56: 121-132 (2010).
Bohm M, Eickelmann M, Li Z, et al., "Detection of functionally active melanocortin receptors and evidence for an immunoregulatory activity of alpha-melanocyte-stimulating hormone in human dermal papilla cells", *Endocrinology*, 146(11): 4635-4646 (Nov. 2005).
Brennesvik EO, Ktori C, Ruzzin J, Jebens E, Shepherd PR, Jensen J., "Adrenaline potentiates insulin-stimulated PKB activation via cAMP and Epac: implications for cross talk between insulin and adrenaline", *Cell Signal.*, 17(12):1551-1559 (Dec. 2005).
Buck et al., "Cytosolic adenylyl cyclase defines a unique signaling molecule in Mammals," *Proc. Natl. Acad. Sci. USA*, 96: 79-84 (1999).
Busca R, Abbe P, Mantoux F, et al., "Ras mediates the cAMP-dependent activation of extracellular signal-regulated kinases (ERKs) in melanocytes", *EMBO J.*, 19(12):2900-2910 (Jun. 15, 2000).
Calipel A, Lefevre G, Pouponnot C, Mouriaux F, Eychene A, Mascarelli F., "Mutation of B-Raf in human choroidal melanoma cells mediates cell proliferation and transformation through the MEK/ERK pathway", *J Biol Chem.*, 278(43): 42409-42418 (Oct. 24, 2003).
*Cancer Facts & Figures*, American Cancer Society, Atlanta, Georgia (2010).
Chen, Y., et al., "Soluble adenylyl cyclase as an evolutionarily conserved bicarbonate sensor", *Science*, 289(5479): 625-8 (2000).
Dalton SR, Gerami P, Kolaitis NA, Charzan S, Werling R, LeBoit PE, Bastian BC., "Use of fluorescence in situ hybridization (FISH) to distinguish intranodal nevus from metastatic melanoma", *Am J Surg Pathol.*, 34(2): 231-7 (Feb. 2010).
Dobroff AS, Wang H, Melnikova VO, Villares GJ, Zigler M, Huang L, Bar-Eli M., "Silencing cAMP-response element-binding protein (CREB) identifies CYR61 as a tumor suppressor gene in melanoma", *J. Biol Chem.*, 284(38): 26194-206 (Sep. 18, 2009).

(Continued)

*Primary Examiner* — Peter J Reddig
(74) *Attorney, Agent, or Firm* — Leydig, Voit & Mayer, Ltd.

(57) ABSTRACT

The invention provides a method for diagnosing a melanocytic proliferation in a subject comprising staining a sample of lesional melanocytes with an antibody against soluble adenylyl cyclase (sAC) and interpreting the sAC staining pattern, which is associated with a diagnosis of a melanocytic proliferation. The sAC staining pattern, which is complex, is discriminatory and distinctive according to the nature of the melanocytic proliferation. The sAC staining pattern comprises one or more of dot-like Golgi staining, broad granular Golgi staining, diffuse cytoplasmic staining, nucleolar staining, incomplete granular nuclear staining, and pan-nuclear staining. The method of the invention is particularly useful in confirming or disaffirming a diagnosis reached through conventional histologic examination of a sample. Additionally, the invention provides a kit for use in interpreting melanocytic proliferations.

11 Claims, 29 Drawing Sheets

(56) References Cited

OTHER PUBLICATIONS

Dumaz N, Hayward R, Martin J, et al., "In melanoma, RAS mutations are accompanied by switching signaling from BRAF to CRAF and disrupted cyclic AMP signaling", *Cancer Res.*, 66(19): 9483-9491 (Oct. 1, 2006).
Dumont et al., *Trends Biochem. Sci.*, 14: 67-71 (1989).
Eves P, Haycock J, Layton C, et al., "Anti-inflammatory and anti-invasive effects of alpha-melanocyte-stimulating hormone in human melanoma cells", *Br J Cancer.*, 89(10): 2004-2015 (Nov. 17, 2003).
Feng Q, Zhang Y, Li Y, Liu Z, Zuo J, Fang F., "Two domains are critical for the nuclear localization of soluble adenylyl cyclase", *Biochimie*, 88(3-4): 319-328 (Mar.-Apr. 2006).
Feng QP, Zuo J, Meng Y, Fang FD., "Nuclear localization region in soluble adenylyl cyclase", Zhongguo Yi Xue Ke Xue Yuan Xue Bao, 27(3):280-284 (Jun. 2005).
Filippa N, Sable CL, Filloux C, Hemmings B, Van Obberghen E., "Mechanism of protein kinase B activation by cyclic AMP-dependent protein kinase", *Mol Cell Biol.*, 19(7): 4989-5000 (Jul. 1999).
Gao L, Feng Y, Bowers R, et al., "Ras-associated protein-1 regulates extracellular signal-regulated kinase activation and migration in melanoma cells: two processes important to melanoma tumorigenesis and metastasis", *Cancer Res.*, 66(16): 7880-7888 (Aug. 15, 2006).
GenBank Accession Record No. AAF65931.1, submitted on Apr. 28, 2003.
Gerami P, Barnhill RL, Beilfuss BA, LeBoit P, Schneider P, Guitart J., "Superficial melanocytic neoplasms with pagetoidmelanocytosis: a study of interobserver concordance and correlation with FISH", *Am J Surg Pathol.*, 34(6): 816-21 (Jun. 2010).
Gerami P, Jewell SS, Morrison LE, Blondin B, Schulz J, Ruffalo T, Matushek P 4th, Legator M, Jacobson K, Dalton SR, Charzan S, Kolaitis NA, Guitart J, Lertsbarapa T, Boone S, LeBoit PE, Bastian BC., "Fluorescence in situ hybridization (FISH) as an ancillary diagnostic tool in the diagnosis of melanoma", *Am J Surg Pathol.*, 33(8):1146-56 (Aug. 2009) Erratum in: *Am J Surg Pathol.*, 34(5): 688 (May 2010).
Gerami P, Mafee M, Lurtsbarapa T, Guitart J, Haghighat Z, Newman M., "Sensitivity of fluorescence in situ hybridization for melanoma diagnosis using RREB1, MYB, Cep6, and 11q13 probes in melanoma subtypes", *Arch Dermatol.*, 146(3): 273-8 (Mar. 2010).
Gerami P, Pouryazdanparast P, Vemula S, Bastian BC., "Molecular analysis of a case of nevus of ota showing progressive evolution to melanoma with intermediate stages resembling cellular blue nevus", *Am J Dermatopathol.*, 32(3): 301-5 (May 2010).
Isaac AK, Lertsburapa T, Pathria Mundi J, Martini M, Guitart J, Gerami P., "Polyploidy in spitz nevi: a not uncommon karyotypic abnormality identifiable by fluorescence in situ hybridization", *Am J Dermatopathol.*, 32(2):144-8 (Apr. 2010).
Jaiswal et al., *J. Biol. Chem.*, 276: 31698-31708 (2001).
Jean D, Bar-Eli M., "Regulation of tumor growth and metastasis of human melanoma by the CREB transcription factor family", *Mol Cell Biochem.*, 212(1-2):19-28 (Sep. 2000).
Kamenetsky, "Mammalian Cells Possess Multiple, Distinctly Regulated cAMP Signaling Cascades," Ph.D. Dissertation, Weill Medical College of Cornell University, Publication No. AAT 3251733 [ProQuest Document ID 1276395511] (2006), Abstract.
Khaled M, Larribere L, Bille K, et al., "Glycogen synthase kinase 3beta is activated by cAMP and plays an active role in the regulation of melanogenesis", *J Biol Chem*, 277(37): 33690-33697 (Sep. 13, 2002).
Lebe B, Pabuççuoğlu U, Ozer E., "The significance of Ki-67 proliferative index and cyclin D1 expression of dysplastic nevi in the biologic spectrum of melanocytic lesions", *Appl Immunohistochem. Mol Morphol*, 15(2):160-4 (Jun. 2007).
Lester BR, Greig RG, Buscarino C, Sheppard JR, Corwin SP, Poste G., "cAMP metabolism in B16 melanoma clones during the formation of experimental and spontaneous metastases", *Int J Cancer*, 38(3): 405-411 (Sep. 15, 1986).

Li Lx, Crotty KA, McCarthy SW, Palmer AA, Kril JJ., "A zonal comparison of MIB1-Ki67 immunoreactivity in benign and malignant melanocytic lesions", *Am J Dermatopathol.*, 22(6): 489-95 (Dec. 2000).
Lissitzky JC, Parriaux D, Ristorcelli E, Verine A, Lombardo D, Verrando P., "Cyclic AMP signaling as a mediator of vasculogenic mimicry in aggressive human melanoma cells in vitro", *Cancer Res.*, 69(3): 802-809 (Feb. 1, 2009).
Magro CM, Crowson AN, Mihm MC, Kline M., "De novo intraepidermalepithelioid melanocytic dysplasia: an emerging entity", *J Cutan Pathol.*, 37(8): 866-9 (Aug. 2010).
Magro et al., "The dermal-based borderline melanocytic tumor: A categorical approach," *J. Acad. Dermatol.*, 62(3): 469-479 (2010).
Magro et al., "The superficial atypical Spitz tumor and malignant melanoma of superficial spreading type arising in association with the superficial atypical Spitz tumor: A distinct form of dysplastic Spitzoid nevomelanocytic proliferation," *J. Acad. Dermatol.*, 60(5): 814-823 (2009).
Mantovani G, Bondioni S, Lania AG, et al., "High expression of PKA regulatory subunit 1A protein is related to proliferation of human melanoma cells", *Oncogene*, 27(13):1834-1843 (Mar. 20, 2008).
Newman MD, Lertsburapa T, Mirzabeigi M, Mafee M, Guitart J, Gerami P., "Fluorescence in situ hybridization as a tool for microstaging in malignant melanoma", *Mod Pathol.*, 22(8): 989-95 (Aug. 2009), Epub May 15, 2009.
Newman MD, Mirzabeigi M, Gerami P., "Chromosomal copy number changes supporting the classification of lentiginousjunctional melanoma of the elderly as a subtype of melanoma", *Mod Pathol.*, 22(9):1258-62 (Sep. 2009), Epub Jun. 19, 2009.
Obara Y, Horgan AM, Stork PJ., "The requirement of Ras and Rap1 for the activation of ERKs by cAMP, PACAP, and KCl in cerebellar granule cells", *J Neurochem.*,101(2): 470-482 (Apr. 2007).
Ohsie et al., *J. Cutan. Pathol.*, 35(5): 433-444 (2008).
Poser I, Bosserhoff AK., "Transcription factors involved in development and progression of malignant melanoma", *Histol Histopathol.*, 19(1):173-188 (Jan. 2004).
Pouryazdanparast P, Newman M, Mafee M, Haghighat Z, Guitart J, Gerami P., "Distinguishing epithelioid blue nevus from blue nevus-like cutaneous melanoma metastasis using fluorescence in situ hybridization", *Am J Surg Pathol.*, 33(9):1396-400 (Sep. 2009).
Rapini RP., "Spitz nevus or melanoma?Semin", *Cutan Med Surg.*, 18(1):56-63 (1999).
Rothberg BE, Moeder CB, Kluger H, Halaban R, Elder DE, Murphy GF, Lazar A, Prieto V, Duncan LM, Rimm DL., "Nuclear to non-nuclear Pmel17/gp100 expression (HMB45 staining) as a discriminator between benign and malignant melanocytic lesions", *Mod Pathol.*, 21(9):1121-9 (Sep. 2008).
Rozengurt et al., *Science*, 234 161-166 (1986).
Rutberg SE, Goldstein IM, Yang YM, Stackpole CW, Ronai Z., "Expression and transcriptional activity of AP-1, CRE, and URE binding proteins in B16 mouse melanoma subclones", *Mol Carcinog.*, 10(2): 82-87 (Jun. 1994).
Sable CL, Filippa N, Hemmings B, Van Obberghen E., "cAMP stimulates protein kinase B in a Wortmannin-insensitive manner", *FEBS Lett.*, 409(2): 253-257 (Jun. 9, 1997).
Sestakova B, Ondrusova L, Vachtenheim J, "Cell cycle inhibitor p21/WAF1/CIP1 as a cofactor of MITF expression in melanoma cells", *Pigment Cell Melanoma Res.*, 23(2): 238-51 (Apr. 2010).
Sheppard JR, Koestler TP, Corwin SP, et al. Experimental metastasis correlates with cyclic AMP accumulation in B16 melanoma clones. *Nature*. Apr. 5-11, 1984;308(5959):544-547.
Sheppard JR, Lester B, Doll J, et al., "Biochemical regulation of adenylate cyclase in murine melanoma clones with different metastatic properties", *Int J Cancer*, 37(5): 713-722 (May 15, 1986).
Sondak, *Cancer J.*, 7 (Suppl. 1): S24-27 (2001).
Soyer et al., "Color Atlas of Melanocytic Lesions of the Skin", p. 23 (Springer-Verlag, Berlin, 2007).

(56) References Cited

OTHER PUBLICATIONS

Vollmer RT., "Patient age in Spitz nevus and malignant melanoma: implication of Bayes rule for differential diagnosis", *Am J Clin Pathol.* 121(6): 872-7 (2004).

Wellbrock C, Rana S, Paterson H, Pickersgill H, Brummelkamp T, Marais R., "Oncogenic BRAF regulates melanoma proliferation through the lineage specific factor MITF", *PLoS One.*, 3(7): e2734 (2008).

Xu X, Elder DE., "A practical approach to selected problematic melanocytic Lesions", *Am J Clin Pathol.*, 121 Suppl:S3-32 (2004).

Zippin JH, Chadwick PA, Levin LR, Buck J, Magro CM., "Soluble adenylyl cyclase defines a nuclear cAMP microdomain in keratinocyte hyperproliferative skin diseases", *J Invest Dermatol.*, 130(5): 1279-1287 (May 2010).

Zippin JH, Chen Y, Nahirney P, et al., "Compartmentalization of bicarbonate-sensitive adenylyl cyclase in distinct signaling microdomains", *FASEB J.*, 17(1): 82-84 (Jan. 2003).

Zippin JH, Farrell J, Huron D, et al., "Bicarbonate-responsive 'soluble' adenylyl cyclase defines a nuclear cAMP microdomain", *J Cell Biol.*, 164(4): 527-534 (Feb. 16, 2004).

* cited by examiner

Lesional melanocyte

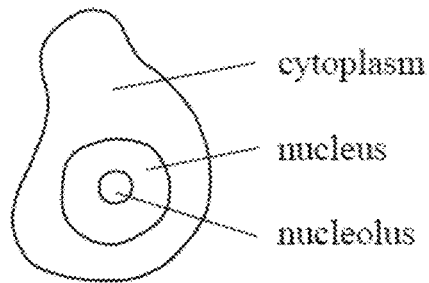
- cytoplasm
- nucleus
- nucleolus

A. Lesional melanocyte with dot-like Golgi staining 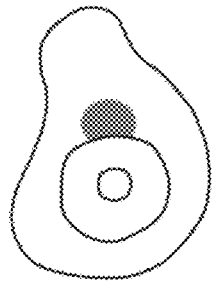

B. Lesional melanocyte with broad granular Golgi staining 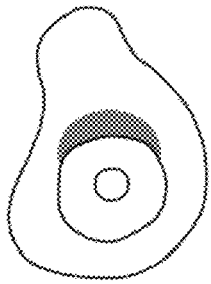

C. Lesional melanocyte with diffuse cytoplasmic staining 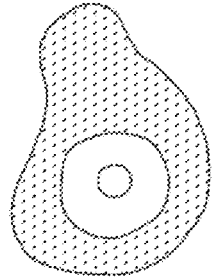

D. Lesional melanocyte with nucleolar staining 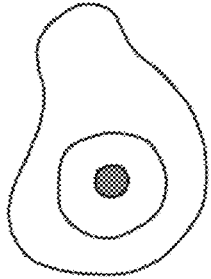

E. Lesional melanocyte with incomplete granular nuclear staining 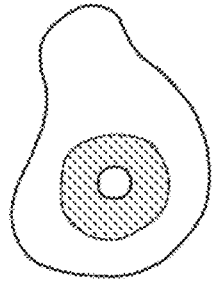

F. Lesional melanocyte with pan-nuclear staining 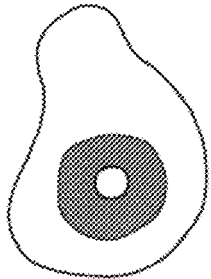

FIG. 29

SEQUENCE LISTING

```
<160> NUMBER OF SEQ ID NOS: 10

<210> SEQ ID NO 1
<211> LENGTH: 1610
<212> TYPE: PRT
<213> ORGANISM: Homo sapiens
<220> FEATURE:
<221> NAME/KEY: MISC_FEATURE
<223> OTHER INFORMATION: sACf1

<400> SEQUENCE: 1

Met Asn Thr Pro Lys Glu Glu Phe Gln Asp Trp Pro Ile Val Arg Ile
1               5                   10                  15

Ala Ala His Leu Pro Asp Leu Ile Val Tyr Gly His Phe Ser Pro Glu
                20                  25                  30

Arg Pro Phe Met Asp Tyr Phe Asp Gly Val Leu Met Phe Val Asp Ile
            35                  40                  45

Ser Gly Phe Thr Ala Met Thr Glu Lys Phe Ser Ser Ala Met Tyr Met
        50                  55                  60

Asp Arg Gly Ala Glu Gln Leu Val Glu Ile Leu Asn Tyr His Ile Ser
65                  70                  75                  80

Ala Ile Val Glu Lys Val Leu Ile Phe Gly Gly Asp Ile Leu Lys Phe
                85                  90                  95

Ala Gly Asp Ala Leu Leu Ala Leu Trp Arg Val Glu Arg Lys Gln Leu
            100                 105                 110

Lys Asn Ile Ile Thr Val Val Ile Lys Cys Ser Leu Glu Ile His Gly
        115                 120                 125

Leu Phe Glu Thr Gln Glu Trp Glu Glu Gly Leu Asp Ile Arg Val Lys
    130                 135                 140

Ile Gly Leu Ala Ala Gly His Ile Ser Met Leu Val Phe Gly Asp Glu
145                 150                 155                 160

Thr His Ser His Phe Leu Val Ile Gly Gln Ala Val Asp Asp Val Arg
                165                 170                 175
```

```
Leu Ala Gln Asn Met Ala Gln Met Asn Asp Val Ile Leu Ser Pro Asn
            180                 185                 190
Cys Trp Gln Leu Cys Asp Arg Ser Met Ile Glu Ile Glu Ser Val Pro
            195                 200             205
Asp Gln Arg Ala Val Lys Val Asn Phe Leu Lys Pro Pro Pro Asn Phe
        210                 215                 220
Asn Phe Asp Glu Phe Phe Thr Lys Cys Thr Thr Phe Met His Tyr Tyr
225                 230                 235                 240
Pro Ser Gly Glu His Lys Asn Leu Leu Arg Leu Ala Cys Thr Leu Lys
                245                 250                 255
Pro Asp Pro Glu Leu Glu Met Ser Leu Gln Lys Tyr Val Met Glu Ser
            260                 265                 270
Ile Leu Lys Gln Ile Asp Asn Lys Gln Leu Gln Gly Tyr Leu Ser Glu
            275                 280                 285
Leu Arg Pro Val Thr Ile Val Phe Val Asn Leu Met Phe Glu Asp Gln
        290                 295                 300
Asp Lys Ala Glu Glu Ile Gly Pro Ala Ile Gln Asp Ala Tyr Met His
305                 310                 315                 320
Ile Thr Ser Val Leu Lys Ile Phe Gln Gly Gln Ile Asn Lys Val Phe
                325                 330                 335
Met Phe Asp Lys Gly Cys Ser Phe Leu Cys Val Phe Gly Phe Pro Gly
            340                 345                 350
Glu Lys Val Pro Asp Glu Leu Thr His Ala Leu Glu Cys Ala Met Asp
            355                 360                 365
Ile Phe Asp Phe Cys Ser Gln Val His Lys Ile Gln Thr Val Ser Ile
        370                 375                 380
Gly Val Ala Ser Gly Ile Val Phe Cys Gly Ile Val Gly His Thr Val
385                 390                 395                 400
Arg His Glu Tyr Thr Val Ile Gly Gln Lys Val Asn Leu Ala Ala Arg
                405                 410                 415
Met Met Met Tyr Tyr Pro Gly Ile Val Thr Cys Asp Ser Val Thr Tyr
            420                 425                 430
Asn Gly Ser Asn Leu Pro Ala Tyr Phe Phe Lys Glu Leu Pro Lys Lys
        435                 440                 445
Val Met Lys Gly Val Ala Asp Ser Gly Pro Leu Tyr Gln Tyr Trp Gly
450                 455                 460
Arg Thr Glu Lys Val Met Phe Gly Met Ala Cys Leu Ile Cys Asn Arg
465                 470                 475                 480
Lys Glu Asp Tyr Pro Leu Leu Gly Arg Asn Lys Glu Ile Asn Tyr Phe
                485                 490                 495
Met Tyr Thr Met Lys Lys Phe Leu Ile Ser Asn Ser Ser Gln Val Leu
            500                 505                 510
Met Tyr Glu Gly Leu Pro Gly Tyr Gly Lys Ser Gln Ile Leu Met Lys
            515                 520                 525
Ile Glu Tyr Leu Ala Gln Gly Lys Asn His Arg Ile Ile Ala Ile Ser
        530                 535                 540
Leu Asn Lys Ile Ser Phe His Gln Thr Phe Tyr Thr Ile Gln Met Phe
545                 550                 555                 560
Met Ala Asn Val Leu Gly Leu Asp Thr Cys Lys His Tyr Lys Glu Arg
                565                 570                 575
Gln Thr Asn Leu Arg Asn Lys Val Met Thr Leu Leu Asp Glu Lys Phe
            580                 585                 590
```

```
Tyr Cys Leu Leu Asn Asp Ile Phe His Val Gln Phe Pro Ile Ser Arg
            595                 600                 605

Glu Ile Ser Arg Met Ser Thr Leu Lys Lys Gln Lys Gln Leu Glu Ile
610                 615                 620

Leu Phe Met Lys Ile Leu Lys Leu Ile Val Lys Glu Glu Arg Ile Ile
625                 630                 635                 640

Phe Ile Ile Asp Glu Ala Gln Phe Val Asp Ser Thr Ser Trp Arg Phe
            645                 650                 655

Met Glu Lys Leu Ile Arg Thr Leu Pro Ile Phe Ile Ile Met Ser Leu
            660                 665                 670

Cys Pro Phe Val Asn Ile Pro Cys Ala Ala Ala Arg Ala Val Ile Lys
            675                 680                 685

Asn Arg Asn Thr Thr Tyr Ile Val Val Gly Ala Val Gln Pro Asn Asp
690                 695                 700

Ile Ser Asn Lys Ile Cys Leu Asp Leu Asn Val Ser Cys Ile Ser Lys
705                 710                 715                 720

Glu Leu Asp Ser Tyr Leu Gly Glu Gly Ser Cys Gly Ile Pro Phe Tyr
            725                 730                 735

Cys Glu Glu Leu Leu Lys Asn Leu Glu His His Glu Val Leu Val Phe
            740                 745                 750

Gln Gln Thr Glu Ser Glu Lys Thr Asn Arg Thr Trp Asn Asn Leu
            755                 760                 765

Phe Lys Tyr Ser Ile Lys Leu Thr Glu Lys Leu Asn Met Val Thr Leu
            770                 775                 780

His Ser Asp Lys Glu Ser Glu Val Cys His Leu Thr Ser Gly Val
785                 790                 795                 800

Arg Leu Lys Asn Leu Ser Pro Pro Thr Ser Leu Lys Glu Ile Ser Leu
            805                 810                 815

Ile Gln Leu Asp Ser Met Arg Leu Ser His Gln Met Leu Val Arg Cys
            820                 825                 830

Ala Ala Ile Ile Gly Leu Thr Phe Thr Thr Glu Leu Leu Phe Glu Ile
            835                 840                 845

Leu Pro Cys Trp Asn Met Lys Met Met Ile Lys Thr Leu Ala Thr Leu
            850                 855                 860

Val Glu Ser Asn Ile Phe Tyr Cys Phe Arg Asn Gly Lys Glu Leu Gln
865                 870                 875                 880

Lys Ala Leu Lys Gln Asn Asp Pro Ser Phe Glu Val His Tyr Arg Ser
                    885                 890                 895

Leu Ser Leu Lys Pro Ser Glu Gly Met Asp His Gly Glu Glu Gln
            900                 905                 910

Leu Arg Glu Leu Glu Asn Glu Val Ile Glu Cys His Arg Ile Arg Phe
            915                 920                 925

Cys Asn Pro Met Met Gln Lys Thr Ala Tyr Glu Leu Trp Leu Lys Asp
            930                 935                 940

Gln Arg Lys Ala Met His Leu Lys Cys Ala Arg Phe Leu Glu Glu Asp
945                 950                 955                 960

Ala His Arg Cys Asp His Cys Arg Gly Arg Asp Phe Ile Pro Tyr His
            965                 970                 975

His Phe Thr Val Asn Ile Arg Leu Asn Ala Leu Asp Met Asp Ala Ile
            980                 985                 990

Lys Lys Met Ala Met Ser His Gly Phe Lys Thr Glu Glu Lys Leu Ile
    995                 1000                1005
```

```
Leu Ser Asn Ser Glu Ile Pro Glu Thr Ser Ala Phe Phe Pro Glu
1010                1015                1020

Asn Arg Ser Pro Glu Glu Ile Arg Glu Lys Ile Leu Asn Phe Phe
1025                1030                1035

Asp His Val Leu Thr Lys Met Lys Thr Ser Asp Glu Asp Ile Ile
1040                1045                1050

Pro Leu Glu Ser Cys Gln Cys Glu Glu Ile Leu Glu Ile Val Ile
1055                1060                1065

Leu Pro Leu Ala His His Phe Leu Ala Leu Gly Glu Asn Asp Lys
1070                1075                1080

Ala Leu Tyr Tyr Phe Leu Glu Ile Ala Ser Ala Tyr Leu Ile Phe
1085                1090                1095

Cys Asp Asn Tyr Met Ala Tyr Met Tyr Leu Asn Glu Gly Gln Lys
1100                1105                1110

Leu Leu Lys Thr Leu Lys Lys Asp Lys Ser Trp Ser Gln Thr Phe
1115                1120                1125

Glu Ser Ala Thr Phe Tyr Ser Leu Lys Gly Glu Val Cys Phe Asn
1130                1135                1140

Met Gly Gln Ile Val Leu Ala Lys Lys Met Leu Arg Lys Ala Leu
1145                1150                1155

Lys Leu Leu Asn Arg Ile Phe Pro Tyr Asn Leu Ile Ser Leu Phe
1160                1165                1170

Leu His Ile His Val Glu Lys Asn Arg His Phe His Tyr Val Asn
1175                1180                1185

Arg Gln Ala Gln Glu Ser Pro Pro Gly Lys Lys Arg Leu Ala
1190                1195                1200

Gln Leu Tyr Arg Gln Thr Val Cys Leu Ser Leu Leu Trp Arg Ile
1205                1210                1215

Tyr Ser Tyr Ser Tyr Leu Phe His Cys Lys Tyr Tyr Ala His Leu
1220                1225                1230

Ala Val Met Met Gln Met Asn Thr Ala Leu Glu Thr Gln Asn Cys
1235                1240                1245

Phe Gln Ile Ile Lys Ala Tyr Leu Asp Tyr Ser Leu Tyr His His
1250                1255                1260

Leu Ala Gly Tyr Lys Gly Val Trp Phe Lys Tyr Glu Val Met Ala
1265                1270                1275

Met Glu His Ile Phe Asn Leu Pro Leu Lys Gly Glu Gly Ile Glu
1280                1285                1290

Ile Val Ala Tyr Val Ala Glu Thr Leu Val Phe Asn Lys Leu Ile
1295                1300                1305

Met Gly His Leu Asp Leu Ala Ile Glu Leu Gly Ser Arg Ala Leu
1310                1315                1320

Gln Met Trp Ala Leu Leu Gln Asn Pro Asn Arg His Tyr Gln Ser
1325                1330                1335

Leu Cys Arg Leu Ser Arg Cys Leu Leu Leu Asn Ser Arg Tyr Pro
1340                1345                1350

Gln Leu Ile Gln Val Leu Gly Arg Leu Trp Glu Leu Ser Val Thr
1355                1360                1365

Gln Glu His Ile Phe Ser Lys Ala Phe Phe Tyr Phe Val Cys Leu
1370                1375                1380

Asp Ile Leu Leu Tyr Ser Gly Phe Val Tyr Arg Thr Phe Glu Glu
1385                1390                1395
```

```
Cys Leu Glu Phe Ile His Gln Tyr Glu Asn Asn Arg Ile Leu Lys
    1400                1405                1410

Phe His Ser Gly Leu Leu Gly Leu Tyr Ser Ser Val Ala Ile
    1415                1420                1425

Trp Tyr Ala Arg Leu Gln Glu Trp Asp Asn Phe Tyr Lys Phe Ser
    1430                1435                1440

Asn Arg Ala Lys Asn Leu Leu Pro Arg Arg Thr Met Thr Leu Thr
    1445                1450                1455

Tyr Tyr Asp Gly Ile Ser Arg Tyr Met Glu Gly Gln Val Leu His
    1460                1465                1470

Leu Gln Lys Gln Ile Lys Glu Gln Ser Glu Asn Ala Gln Ala Ser
    1475                1480                1485

Gly Glu Glu Leu Leu Lys Asn Leu Glu Asn Leu Val Ala Gln Asn
    1490                1495                1500

Thr Thr Gly Pro Val Phe Cys Pro Arg Leu Tyr His Leu Met Ala
    1505                1510                1515

Tyr Val Cys Ile Leu Met Gly Asp Gly Gln Lys Cys Gly Leu Phe
    1520                1525                1530

Leu Asn Thr Ala Leu Arg Leu Ser Glu Thr Gln Gly Asn Ile Leu
    1535                1540                1545

Glu Lys Cys Trp Leu Asn Met Asn Lys Glu Ser Trp Tyr Ser Thr
    1550                1555                1560

Ser Glu Leu Lys Glu Asp Gln Trp Leu Gln Thr Ile Leu Ser Leu
    1565                1570                1575

Pro Ser Trp Glu Lys Ile Val Ala Gly Arg Val Asn Ile Gln Asp
    1580                1585                1590

Leu Gln Lys Asn Lys Phe Leu Met Arg Ala Asn Thr Val Asp Asn
    1595                1600                1605

His Phe
    1610

<210> SEQ ID NO 2
<211> LENGTH: 470
<212> TYPE: PRT
<213> ORGANISM: Homo sapiens
<220> FEATURE:
<221> NAME/KEY: MISC_FEATURE
<223> OTHER INFORMATION: sACt

<400> SEQUENCE: 2

Met Asn Thr Pro Lys Glu Glu Phe Gln Asp Trp Pro Ile Val Arg Ile
1               5                   10                  15

Ala Ala His Leu Pro Asp Leu Ile Val Tyr Gly His Phe Ser Pro Glu
                20                  25                  30

Arg Pro Phe Met Asp Tyr Phe Asp Gly Val Leu Met Phe Val Asp Ile
            35                  40                  45

Ser Gly Phe Thr Ala Met Thr Glu Lys Phe Ser Ser Ala Met Tyr Met
        50                  55                  60

Asp Arg Gly Ala Glu Gln Leu Val Glu Ile Leu Asn Tyr His Ile Ser
65                  70                  75                  80

Ala Ile Val Glu Lys Val Leu Ile Phe Gly Gly Asp Ile Leu Lys Phe
                85                  90                  95

Ala Gly Asp Ala Leu Leu Ala Leu Trp Arg Val Glu Arg Lys Gln Leu
            100                 105                 110

Lys Asn Ile Ile Thr Val Val Ile Lys Cys Ser Leu Glu Ile His Gly
        115                 120                 125
```

```
Leu Phe Glu Thr Gln Glu Trp Glu Glu Gly Leu Asp Ile Arg Val Lys
    130                 135                 140

Ile Gly Leu Ala Ala Gly His Ile Ser Met Leu Val Phe Gly Asp Glu
145                 150                 155                 160

Thr His Ser His Phe Leu Val Ile Gly Gln Ala Val Asp Asp Val Arg
                165                 170                 175

Leu Ala Gln Asn Met Ala Gln Met Asn Asp Val Ile Leu Ser Pro Asn
                180                 185                 190

Cys Trp Gln Leu Cys Asp Arg Ser Met Ile Glu Ile Glu Ser Val Pro
            195                 200                 205

Asp Gln Arg Ala Val Lys Val Asn Phe Leu Lys Pro Pro Asn Phe
210                 215                 220

Asn Phe Asp Glu Phe Phe Thr Lys Cys Thr Thr Phe Met His Tyr Tyr
225                 230                 235                 240

Pro Ser Gly Glu His Lys Asn Leu Leu Arg Leu Ala Cys Thr Leu Lys
                245                 250                 255

Pro Asp Pro Glu Leu Glu Met Ser Leu Gln Lys Tyr Val Met Glu Ser
                260                 265                 270

Ile Leu Lys Gln Ile Asp Asn Lys Gln Leu Gln Gly Tyr Leu Ser Glu
            275                 280                 285

Leu Arg Pro Val Thr Ile Val Phe Val Asn Leu Met Phe Glu Asp Gln
            290                 295                 300

Asp Lys Ala Glu Glu Ile Gly Pro Ala Ile Gln Asp Ala Tyr Met His
305                 310                 315                 320

Ile Thr Ser Val Leu Lys Ile Phe Gln Gly Gln Ile Asn Lys Val Phe
                325                 330                 335

Met Phe Asp Lys Gly Cys Ser Phe Leu Cys Val Phe Gly Phe Pro Gly
                340                 345                 350

Glu Lys Val Pro Asp Glu Leu Thr His Ala Leu Glu Cys Ala Met Asp
            355                 360                 365

Ile Phe Asp Phe Cys Ser Gln Val His Lys Ile Gln Thr Val Ser Ile
            370                 375                 380

Gly Val Ala Ser Gly Ile Val Phe Cys Gly Ile Val Gly His Thr Val
385                 390                 395                 400

Arg His Glu Tyr Thr Val Ile Gly Gln Lys Val Asn Leu Ala Ala Arg
                405                 410                 415

Met Met Met Tyr Tyr Pro Gly Ile Val Thr Cys Asp Ser Val Thr Tyr
                420                 425                 430

Asn Gly Ser Asn Leu Pro Ala Tyr Phe Phe Lys Glu Leu Pro Lys Lys
            435                 440                 445

Val Met Lys Gly Val Ala Asp Ser Gly Pro Leu Tyr Gln Tyr Trp Gly
450                 455                 460

Arg Thr Glu Lys Val Met
465                 470

<210> SEQ ID NO 3
<211> LENGTH: 50
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R40 and R33
```

```
<400> SEQUENCE: 3

Met Phe Val Asp Ile Ser Gly Phe Thr Ala Met Thr Glu Lys Phe Ser
1               5                   10                  15

Ser Ala Met Tyr Met Asp Arg Gly Ala Glu Gln Leu Val Glu Ile Leu
            20                  25                  30

Asn Tyr His Ile Ser Ala Ile Val Glu Lys Val Leu Ile Phe Gly Gly
        35                  40                  45

Asp Ile
    50

<210> SEQ ID NO 4
<211> LENGTH: 50
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R7, R21, and R53

<400> SEQUENCE: 4

Asp Asp Val Arg Leu Ala Gln Asn Met Ala Gln Met Asn Asp Val Ile
1               5                   10                  15

Leu Ser Pro Asn Cys Trp Gln Leu Cys Asp Arg Ser Met Ile Glu Ile
            20                  25                  30

Glu Ser Val Pro Asp Gln Arg Ala Val Lys Val Asn Phe Leu Lys Pro
        35                  40                  45

Pro Pro
    50

<210> SEQ ID NO 5
<211> LENGTH: 42
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R5, R6.2, R14, R37, R41, R47.1, R52, R54, and
      R59

<400> SEQUENCE: 5

Ser Val Thr Tyr Asn Gly Ser Asn Leu Pro Ala Tyr Phe Phe Lys Glu
1               5                   10                  15

Leu Pro Lys Lys Val Met Lys Gly Val Ala Asp Ser Gly Pro Leu Tyr
            20                  25                  30

Gln Tyr Trp Gly Arg Thr Glu Lys Val Met
        35                  40

<210> SEQ ID NO 6
<211> LENGTH: 16
<212> TYPE: PRT
<213> ORGANISM: Homo sapiens
<220> FEATURE:
<221> NAME/KEY: MISC_FEATURE
<223> OTHER INFORMATION: peptide sequence containing the epitope of
      antibody R33

<400> SEQUENCE: 6

Ala Met Tyr Met Asp Arg Gly Ala Glu Gln Leu Val Glu Ile Leu Asn
1               5                   10                  15
```

```
<210> SEQ ID NO 7
<211> LENGTH: 14
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R7, R21, and R53

<400> SEQUENCE: 7

Glu Ile Glu Ser Val Pro Asp Gln Arg Ala Val Lys Val Asn
1               5                   10

<210> SEQ ID NO 8
<211> LENGTH: 15
<212> TYPE: PRT
<213> ORGANISM: Homo sapiens
<220> FEATURE:
<221> NAME/KEY: MISC_FEATURE
<223> OTHER INFORMATION: peptide sequence containing the epitope of
      antibody R37

<400> SEQUENCE: 8

Glu Leu Pro Lys Lys Val Met Lys Gly Val Ala Asp Ser Gly Pro
1               5                   10                  15

<210> SEQ ID NO 9
<211> LENGTH: 16
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R5 and R37

<400> SEQUENCE: 9

Asn Leu Pro Ala Tyr Phe Phe Lys Glu Leu Pro Lys Lys Val Met Lys
1               5                   10                  15

<210> SEQ ID NO 10
<211> LENGTH: 17
<212> TYPE: PRT
<213> ORGANISM: Homo sapiens
<220> FEATURE:
<221> NAME/KEY: MISC_FEATURE
<223> OTHER INFORMATION: peptide sequence containing the epitopes of
      anti-sAC antibodies R6.2, R14, R37, R41, R41.7, R52, R54, and R59

<400> SEQUENCE: 10

Met Lys Gly Val Ala Asp Ser Gly Pro Leu Tyr Gln Tyr Trp Gly Arg
1               5                   10                  15

Thr
```

METHOD FOR DIAGNOSING MELANOCYTIC PROLIFERATIONS

CROSS-REFERENCE TO RELATED APPLICATIONS

This application claims the benefit of U.S. Provisional Patent Application No. 61/326,174, filed Apr. 20, 2010, the entire content of which is incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,960 Byte ASCII (Text) file named "711361_ST25.TXT," created on Oct. 16, 2012.

BACKGROUND OF THE INVENTION

Melanocytes, i.e., pigment-producing cells in the skin, eye, and mucosal surfaces, give rise to a spectrum of proliferative lesions ranging from benign nevi to overtly malignant melanoma. Melanoma is a disease with high metastatic potential even at very early stages of development. Melanoma accounts for less than 5% of skin cancer cases, but causes a large majority of skin cancer deaths (*Cancer Facts & Figures*, American Cancer Society, Atlanta, Ga. (2010)). Melanoma is notorious for its resistance to chemotherapy and radiotherapy (Sondak, *Cancer J.*, 7 (*Suppl.* 1): S24-27 (2001)), so early, accurate diagnosis of melanocytic proliferations remains the key to reducing morbidity and mortality.

Unfortunately, melanocytic lesions exhibit striking heterogeneity in terms of morphology and biologic behavior, which can make their diagnosis challenging for even the most experienced dermatopathologists. Lesions that are neither clearly benign nor clearly malignant have been historically grouped as "melanocytic tumors of uncertain malignant potential ("MELTUMP"). Progress has been made in developing objective histologic criteria for the diagnosis of these indeterminate lesions (Magro et al., *J. Am. Acad. Dermatol.*, 62(3): 469-479 (2010)), but inconclusive diagnoses may still affect the clinical management of patients, who may be subjected to unnecessarily aggressive surgery, adjuvant treatments, chemotherapy, immunotherapy, or radiation therapy.

Although histologic examination of tissue biopsies remains the gold standard in the diagnosis of melanocytic proliferations (Soyer et al., *Color Atlas of Melanocytic Lesions of the Skin*, p. 23 (Springer-Verlag, Berlin, 2007)), the clinical value of adjunct diagnostic techniques is becoming increasingly realized. Information about the genetic make-up and/or protein expression patterns of a lesion can be used to confirm or disaffirm a diagnosis reached through histologic examination.

Examples of adjunct diagnostic techniques include comparative genomic hybridization (CGH), fluorescence in situ hybridization (FISH), and immunostains. CGH and FISH make use of DNA probes to provide information about genetic aberrations in a tissue sample (Blokx et al., *Histopathol.*, 56: 121-132 (2010)). Both FISH and CGH, however, are labor-intensive and time-consuming and require specialized equipment and high-quality tissue samples. Their utility in a clinical setting is accordingly limited. Immunostaining involves the binding of a labeled antibody to a specific protein epitope within a tissue sample, yielding information about protein expression levels or localization. Stains for HMB45, a cytoplasmic premelanosomal glycoprotein, or Ki67, a protein associated with cellular proliferation and ribosomal RNA transcription, are occasionally used in the diagnosis of melanocytic proliferations, although neither stain is absolutely specific nor especially sensitive (Ohsie et al., *J. Cutan. Pathol.*, 35(5): 433-444 (2008)).

Current methods for detection, diagnosis, prognosis, and treatment of melanoma fail to satisfactorily reduce the morbidity and mortality associated with the disease. There is thus a need in the art for additional diagnostic techniques to use in conjunction with traditional histology, particularly diagnostic techniques that are fast, cost-effective, and easy to interpret.

BRIEF SUMMARY OF THE INVENTION

The invention provides a method for diagnosing a melanocytic proliferation in a subject comprising staining a sample of lesional melanocytes with an antibody against soluble adenylyl cyclase (sAC) and interpreting the sAC staining pattern, which is associated with a diagnosis of a melanocytic proliferation. Application of this method yields characteristic staining sAC patterns, which are complex, but appear discriminatory and distinctive according to the nature of the melanocytic proliferation. The sAC staining pattern comprises one or more of dot-like Golgi staining, broad granular Golgi staining, diffuse cytoplasmic staining, nucleolar staining, incomplete granular nuclear staining, and pan-nuclear staining. The invention is intended for use in confirming or disaffirming a diagnosis reached through conventional histologic examination of a sample. In some cases, however, interpretation of sAC staining pattern alone may be sufficient to reach a diagnosis. Additionally, the invention provides a kit for use in interpreting melanocytic proliferations.

DESCRIPTION OF THE DRAWINGS

FIG. 29 is a schematic representation of the six major sAC staining patterns, namely lesional melanocyte with (A) dot-like Golgi staining, (B) broad granular Golgi staining, (c) diffuse cytoplamic staining, (D) nuclear staining, (E) incomplete granular nuclear staining, and (F) pan-nuclear staining.

DETAILED DESCRIPTION OF THE INVENTION

Figure 1:
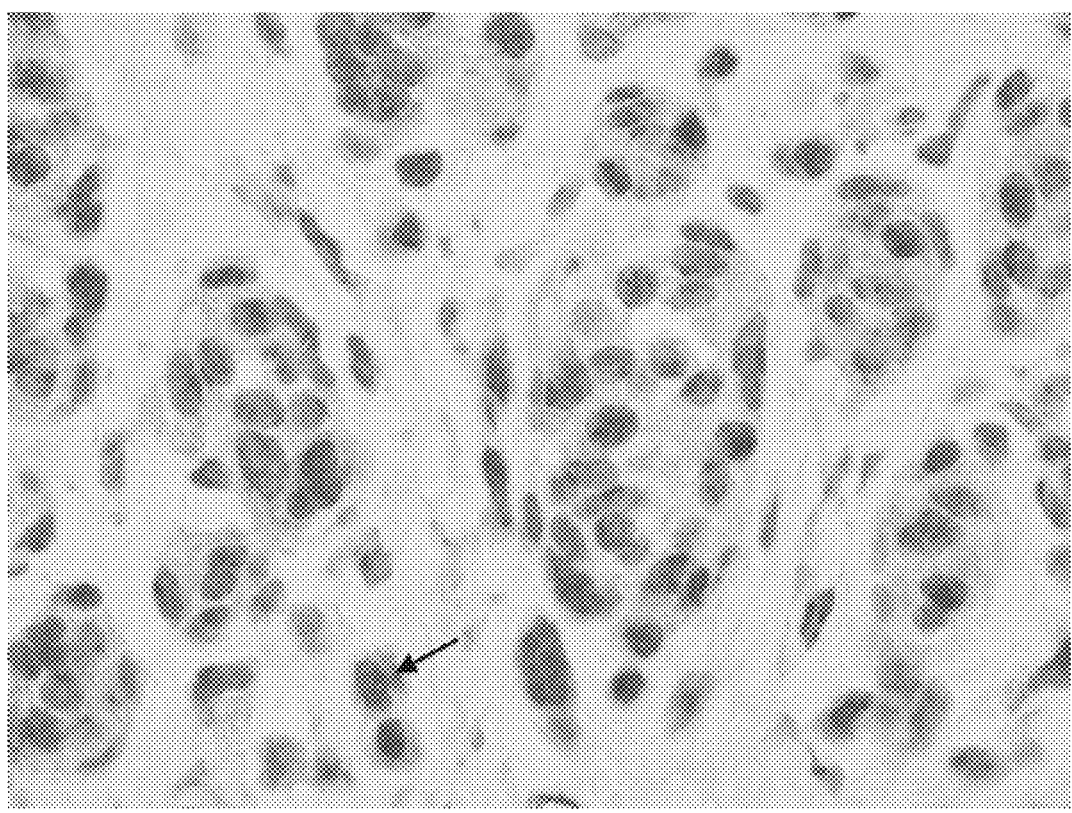
FIG. 1 is a photograph depicting a sAC staining pattern of a benign nevus. The sAC staining pattern is characterized by small dot-like Golgi positivity around the nucleus (arrow). Pan-nuclear staining is not observed. Weak, incomplete granular nuclear staining is sometimes present.

The invention provides a method for diagnosing a melanocytic proliferation in a subject comprising staining a sample of lesional melanocytes with an antibody against soluble adenylyl cyclase (sAC) and interpreting the sAC staining pattern, which is associated with a diagnosis of a melanocytic proliferation. Application of this method yields characteristic staining sAC patterns, which are complex, but appear discriminatory and distinctive according to the nature of the melanocytic proliferation. The sAC staining pattern comprises one or more of dot-like Golgi staining, broad granular Golgi staining, diffuse cytoplasmic staining, nucleolar staining, incomplete granular nuclear staining, and pan-nuclear staining.

The invention is especially intended for use in confirming or disaffirming a diagnosis reached through conventional histologic examination of a sample. In some cases, however, interpretation of sAC staining pattern alone may be sufficient to reach a diagnosis.

sAC is a soluble signaling enzyme that produces cyclic AMP (cAMP), as described in International Patent Application Publication No. WO 2001/085753 and U.S. Pat. No. 6,544,768. The expression of sAC has been observed in keratinocytes, melanocytes, mononuclear cells, eccrine ducts, and nerves of human skin (Zippin et al., *J. Invest. Dermatol.*, 130: 1279-1287 (2010)), in addition to other regions of the body. cAMP mediates cellular responses to nutritional conditions and extracellular signals and has long been known to exert both stimulatory and inhibitory effects on cell growth and proliferation (Dumont et al., *Trends Biochem. Sci.*, 14: 67-71 (1989); Rozengurt et al., *Science*, 234 161-166 (1986)).

The presence or absence of sAC in a tissue sample may be determined by staining the sample with an antibody against sAC. As used herein, "sample" or "biopsy" refers to a biological specimen removed from a subject for diagnostic analysis. In a preferred embodiment, the subject is a human. Typically, the sample comprises a skin biopsy of a body region containing lesional melanocytes. The sample may be derived from a "punch," "shave," curettage, fine needle aspirate, sentinel lymph node, or excisional biopsy, or any other method of biopsy. Typically, the sample will be formalin-fixed and/or paraffin-embedded for ease of handling. Additionally, as used herein, "staining" or "immunostaining" refers to (i) contacting a sample suspected to contain sAC antigenic components with an antibody specific for a sAC antigen, extracellular or intracellular, under conditions in which a stable antigen-antibody complex can form between the antibody and the antigenic components in the sample; and (ii) detecting any antigen-antibody complex formed in step (i) using any suitable means known in the art, wherein the detection of a complex indicates the presence of sAC antigenic components in the sample.

The antibody against sAC, i.e., anti-sAC antibody, can be any antibody, or fragment or derivative thereof, that binds to sAC. The antibody against sAC can be a polyclonal antibody, a monoclonal antibody, a chimeric antibody, a single chain of an antibody, or a Fab fragment that binds to sAC. For example, the antibody against sAC can be a monoclonal antibody directed against a single sAC epitope, a combination of monoclonal antibodies directed against different epitopes of a single sAC antigenic component, monoclonal antibodies directed towards epitopes of different sAC antigenic components, polyclonal antibodies directed towards the same sAC antigen, or polyclonal antibodies directed towards different sAC antigens The antibody can target any epitope of any splice variant of sAC. sAC has several splice variants, including a 48 kDa variant and a 187 kDa variant (Buck et al., *Proc. Natl. Acad. Sci. USA*, 96: 79-84 (1999); Jaiswal et al., *J. Biol. Chem.*, 276: 31698-31708 (2001)). Additional splice variants may also exist. The amino acid sequences of full length sAC (sACfl) and truncated sAC (sACt) are set forth as SEQ ID NO: 1 and SEQ ID NO: 2, respectively.

The antibody against sAC can be prepared by any suitable manner.

A polyclonal antibody can be prepared by immunizing a host animal, e.g., by injection, with the sAC polypeptide or a derivative (e.g., fragment or fusion protein) thereof. Suitable host animals include, but are not limited to, rabbits, mice, rats, sheep, goats, etc. A sAC polypeptide can be produced recombinantly or by chemical synthesis, and a fragment or other derivative thereof, including a fusion protein, can be used as an immunogen to generate an antibody that recognizes the sAC polypeptide. In one embodiment, the sAC polypeptide or fragment thereof can be conjugated to an immunogenic carrier, e.g., bovine serum albumin (BSA) or keyhole limpet hemocyanin (KLH). Adjuvants can be used to increase the immunological response of the host animal, depending on the host species, including but not limited to Freund's (complete and incomplete), mineral gels (such as aluminum hydroxide), surface active substances (such as lysolecithin), pluronic polyols, polyanions, peptides, oil emulsions, keyhole limpet hemocyanins, dinitrophenol, and human adjuvants (such as BCG (bacille Calmette-Guerin) and *Corynebacterium parvum*).

A monoclonal antibody can be prepared by any technique that provides an antibody by a continuous cell line in culture can be used. These techniques include, but are not limited to, the hybridoma technique originally developed by Kohler and Milstein (*Nature*, 256: 495-497 (1975)), as well as the trioma technique, the human B-cell hybridoma technique (Kozbor et al., *Immunol. Today*, 4: 72 (1983); Cote et al., *Proc. Natl. Acad. Sci. USA*, 80: 2026-2030 (1983)), and the EBV hybridoma technique (Cole et al., "The EBV-hybridoma technique and its application to human lung cancer" in *Monoclonal Antibodies and Cancer Therapy*, Alan R. Liss, Inc., pp. 77-96 (1985)). The production of monoclonal antibodies by CDR grafting is described in U.S. Pat. Nos. 5,585,089, 5,693,761, 5,693,762, and 5,225,539. Additionally, monoclonal antibodies can be produced in germ-free animals, as described in International Patent Application Publication No. WO 1989/012690.

A chimeric antibody can be prepared, for example, by splicing the genes from a mouse antibody specific for a sAC polypeptide together with genes from a human antibody of appropriate biological activity (Morrison et al., *J. Bacteria*, 159: 870 (1984); Neuberger et al., *Nature*, 312: 604-608 (1984); and Takeda et al., *Nature*, 314: 452-454 (1985)). Techniques for the production of single chain antibodies (as described in, for example, U.S. Pat. Nos. 5,476,786, 5,132, 405, and 4,946,778) can be adapted to produce an antibody against sAC.

An antibody fragment, which contains the idiotype of the antibody against sAC, can be generated in any suitable manner, e.g., using known techniques. Suitable antibody fragments include, but are not limited to, a F(ab')2 fragment which can be produced by pepsin digestion of the antibody molecule, a Fab' fragment which can be generated by reducing the disulfide bridges of the F(ab')2 fragment, and a Fab fragment which can be generated by treating an antibody with papain and a reducing agent.

The antibody against sAC, as bound to sAC present in the sample, is detected so as to obtain or discern the sAC staining pattern. The detection of the antibody against sAC can be accomplished by any suitable technique, many of which are well known in the art, e.g., enzyme (alkaline phosphatase, horseradish peroxidase, etc.) or fluorophore (FITC, TRITC, AMCA, etc.) mediated techniques. In one embodiment, antibody binding is detected by detecting a label on the antibody against sAC. In another embodiment, the primary antibody is detected by detecting binding of a secondary antibody or reagent to the primary antibody, wherein, in a further embodiment, the secondary antibody is labeled and detected.

Any suitable label can be utilized so as to obtain or discern the sAC staining pattern. Suitable labels include, but are not limited to, enzyme-based, fluorescent, chemiluminescent, radioactive, and dye molecules. Other reagents and materials can be utilized to obtain or discern the sAC staining pattern, such as dewaxing components to dewax paraffin-embedded samples, pretreatment and blocking reagents, amplification reagents, wash buffers, blocking reagents, and co-staining reagents.

A number of anti-sAC antibodies have been identified, including, R5, R6.2, R7, R14, R21, R33, R37, R40, R41, R47.1, R52, R53, R54, and R59 (Kamenetsky, "Mammalian Cells Possess Multiple, Distinctly Regulated cAMP Signaling Cascades," Ph.D. Dissertation, Weill Medical College of Cornell University, Publication No. AAT 3251733 [ProQuest Document ID 1276395511] (2006)). The target epitopes of these antibodies are provided in SEQ ID NOS: 3-10. A preferred embodiment involves the use of the R21 antibody, which is a mouse monoclonal antibody directed against amino acids 203-216 of human sACfl protein (Zippin et al., *J. Invest. Dermatol.*, 130(5): 1279-1287 (2010)).

The staining of a sample of lesional melanocytes with an antibody against sAC yields an sAC staining pattern. As used herein, "staining pattern," "expression pattern," or simply "pattern" refers to the localization of sAC within a cell, as visualized using any of the aforementioned antibody staining techniques. The "sAC staining pattern" comprises dot-like Golgi staining, broad granular Golgi staining, diffuse cytoplasmic staining, nucleolar staining, incomplete granular nuclear staining, and/or pan-nuclear staining. FIG. 29 is a schematic representation of these six major sAC staining patterns. Additional staining features, such as "weak" or "intense" staining, also can be considered as part of the analysis of the sAC staining pattern.

The sAC staining pattern can be associated with a diagnosis of a type of melanocytic proliferation, including a diagnosis selected from the group consisting of benign nevus, benign capsular nevus, atypical nevus of special sites, dysplastic nevus, conventional atypical Spitz tumor, superficial atypical Spitz tumor, borderline deep penetrating nevus-like lesion, nevoid borderline tumor, lentigo maligna melanoma, acral lentiginous melanoma, superficial spreading melanoma, nodular melanoma, and metastatic melanoma. However, it should be appreciated that diagnostic terminology is not completely standardized in the field of this invention. Examples of alternative nomenclature are provided for each diagnosis, but should not be considered comprehensive nor limiting.

This invention is particularly useful in the diagnosis of melanocytic proliferations that are clinically and/or histologically ambiguous. In a preferred embodiment, the sAC staining pattern is used to distinguish between a benign neoplasm and a malignant neoplasm. In another preferred embodiment, the sAC staining pattern is used to distinguish between a diagnosis of dysplastic nevus and a diagnosis of superficial spreading melanoma. In another preferred embodiment, the sAC staining pattern is used to distinguish between a diagnosis of superficial atypical Spitz tumor and a diagnosis of superficial spreading melanoma. In another preferred embodiment, the sAC staining pattern is used to distinguish between a diagnosis of benign capsular nevus and a diagnosis of metastatic melanoma. This invention also can be useful in the assessment of proliferative nodules in congenital nevi, the evaluation of lentigo maligna melanoma margins, the delineation of invasive melanoma from residual nevus cells, and the evaluation of the prognostically indeterminate melanocytic proliferations.

The following sections describe the various types of melanocytic proliferations, including their alternative nomenclature, histologic features, and sAC staining patterns. Additional variations in diagnostic terminology, familiar to one of skill in the art, are also included within the scope of this invention. Histologic features are derived from *The Melanocytic Proliferations: A Comprehensive Textbook of Pigmented Lesions* (Crowson et al., Wiley-Liss, Inc. (2001)), Magro et al., "The superficial atypical Spitz tumor and malignant melanoma of superficial spreading type arising in association with the superficial atypical Spitz tumor: A distinct form of dysplastic Spitzoid nevomelanocytic proliferation," *J. Acad. Dermatol.*, 60(5): 814-823 (2009), and Magro et al., "The dermal-based borderline melanocytic tumor: A categorical approach," *J. Acad. Dermatol.*, 62(3): 469-479 (2010), all of which are incorporated herein by reference.

The terms "melanocytic lesion," "melanocytic proliferation," "melanocytic neoplasm," and "pigmented lesion" are used interchangeably and refer to an accumulation of melanocytes. "Benign" refers to neoplasms that are non-cancerous and lack the ability to metastasize. "Malignant" refers to neoplasms that are cancerous and have the ability to metastasize. All technical and scientific terms used herein have the meaning commonly understood by a person skilled in the art to which this invention belongs.

Benign Nevus

Alternative nomenclature: A benign nevus may also be referred to as a benign acquired nevus, a common acquired nevus, a congenital nevus, a melanocytic nevus, a nondysplastic nevus, a junctional nevus, a dermal nevus, a compound nevus, a mole, or a hamartoma.

Histologic features: A benign nevus is composed of nevomelanocytes and lacks the atypia characteristic of intermediate or malignant melanocytic proliferations. Nevomelanocytes may be classified as type A, type B, or type C and are located in the epidermis and dermis, either in cohesive nests or as singly disposed cells. Type A nevomelanocytes are coarsely melanized, particularly in their dendrites, and more intensely melanized around the nucleus. Nucleoli are tiny and manifest a blue coloration in hematoxylin and eosin preparations. Type A cells are found with the epidermis and superficial dermis. Type B nevomelanocytes are round or cuboidal, nonpigmented cells with round hyperchromatic nuclei containing inconspicuous nucleoli and with a scant rim of eosinophilic cytoplasm. Type B cells most closely resemble the morphology of mononuclear hematopoieitic cells, i.e., small lymphocytes or mast cells, although they are typically slightly larger, being in the 8-10 m size range. Type C nevomelanocytes have a spindled morphology with fibrillary elongate cytoplasmic processes most reminiscent of a mature Schwann cell.

Figure 2:
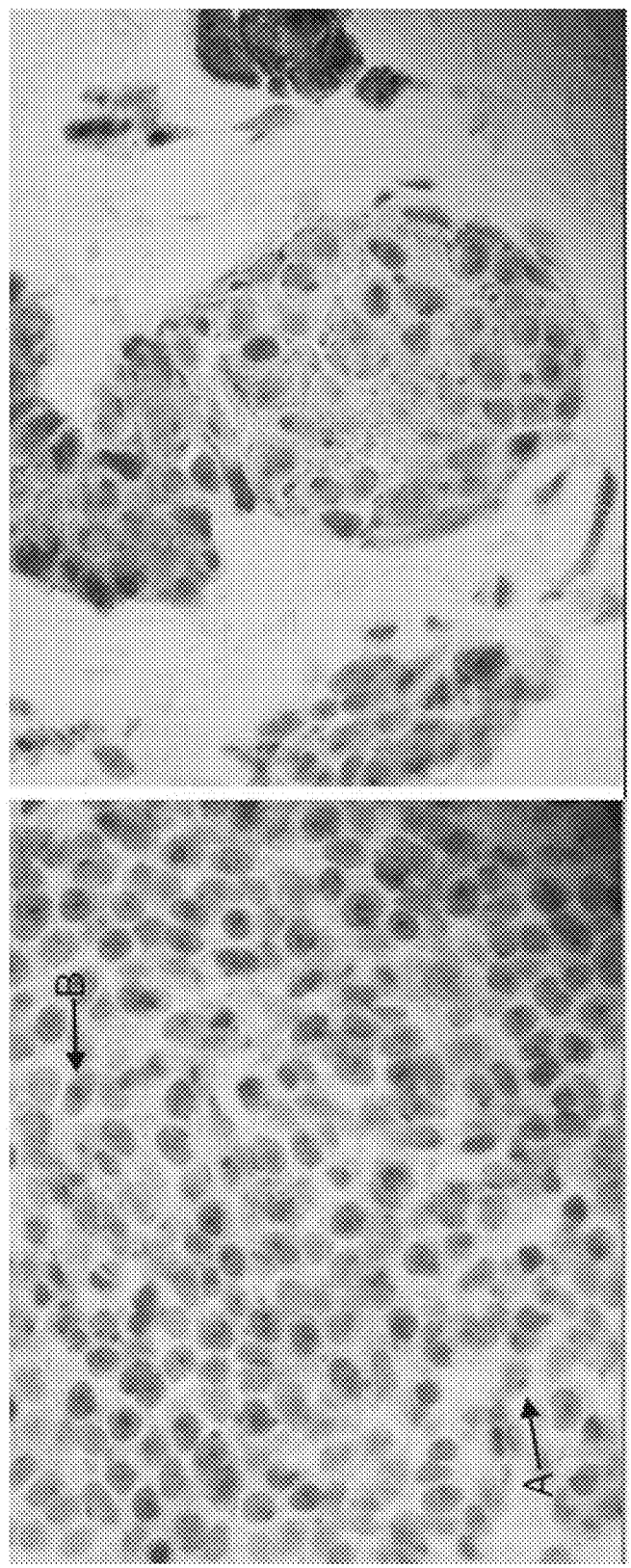
FIG. 2 is a photograph depicting a sAC staining pattern of a benign nevus. The sAC staining pattern is characterized by small dot-like Golgi positivity around the nucleus (arrow A). Pan-nuclear staining is not observed. Weak, incomplete granular nuclear staining is present (arrow B).
Figure 3:
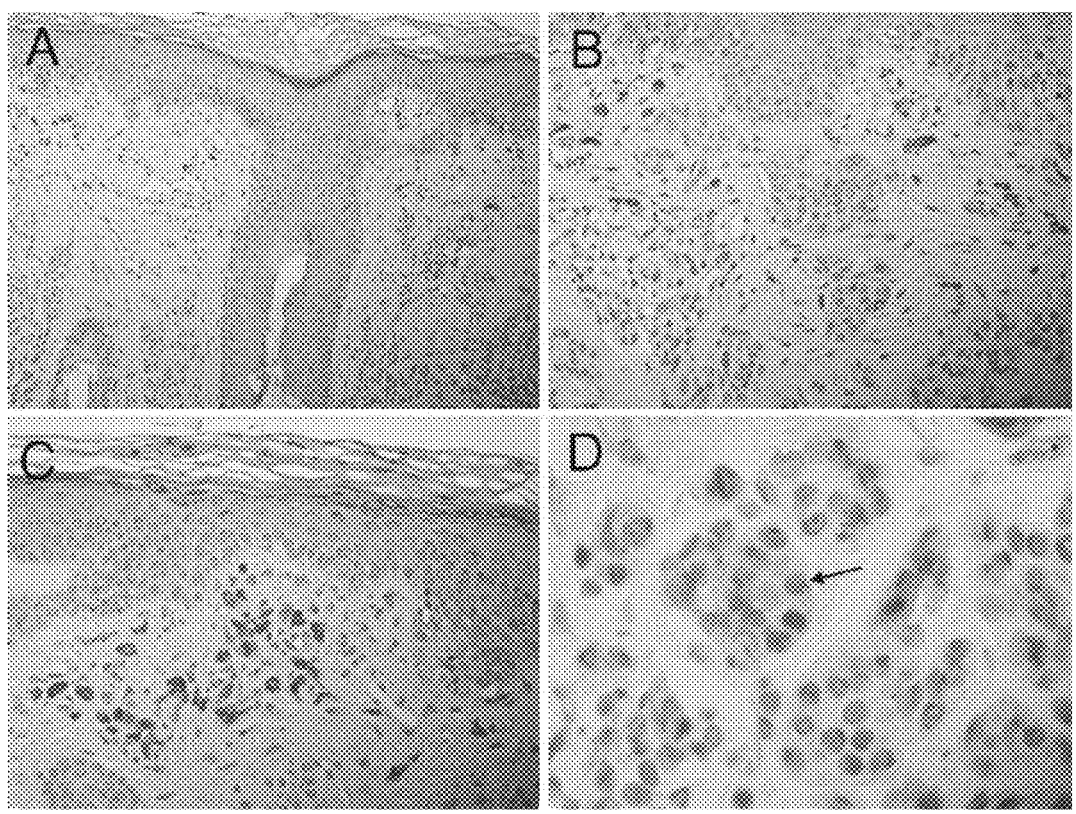
FIG. 3 is a photograph depicting a sAC staining pattern of a recurrent nevus. (A-C) The intraepidermal and dermal components are associated with some component of low-grade atypia as seen within the spectrum of recurrent nevus phenomenon with concomitant inflammation and fibrosis. (D) The sAC pattern is typical for a benign nevus showing the classic dot-like staining pattern around the nucleus (arrow). Significant nuclear staining is not noted.

Prototypic benign nevi show a characteristic pattern of evolution. Lesions initially manifest as lentiginous proliferations of single cells, dispersed along the basal layer of epidermis, forming nonpalpable tan-colored or dark macules, sometimes with an irregular contour. Within the epidermis, discrete junctional theques accumulate to form junctional nevi. A compound nevus, with melanocytes in the epidermis and dermis, forms as migration into the dermis occurs, the clinical concomitant being a palpable, slightly elevated lesion. Complete migration into the dermis results in a dermal nevus, manifested clinically as a palpable lesion with diminishing pigmentation, imparting a tan or pale coloration to the lesion.

sAC staining patterns: Benign nevi show a monotypic pattern of discrete dot-like perinuclear Golgi staining (FIG. 1, arrow) in the majority of melanocytes within the epidermis and dermis (FIGS. 1-3). Nucleolar staining can be seen and is usually weak. Some cases also show focal weak granular nuclear staining. Most cases do not exhibit any pan-nuclear staining, but rare cells with this particular staining pattern may be observed.

Benign Capsular Nevus

Alternative nomenclature: A benign capsular nevus may also be referred to as a collection of benign nevus cells.

Figure 26:
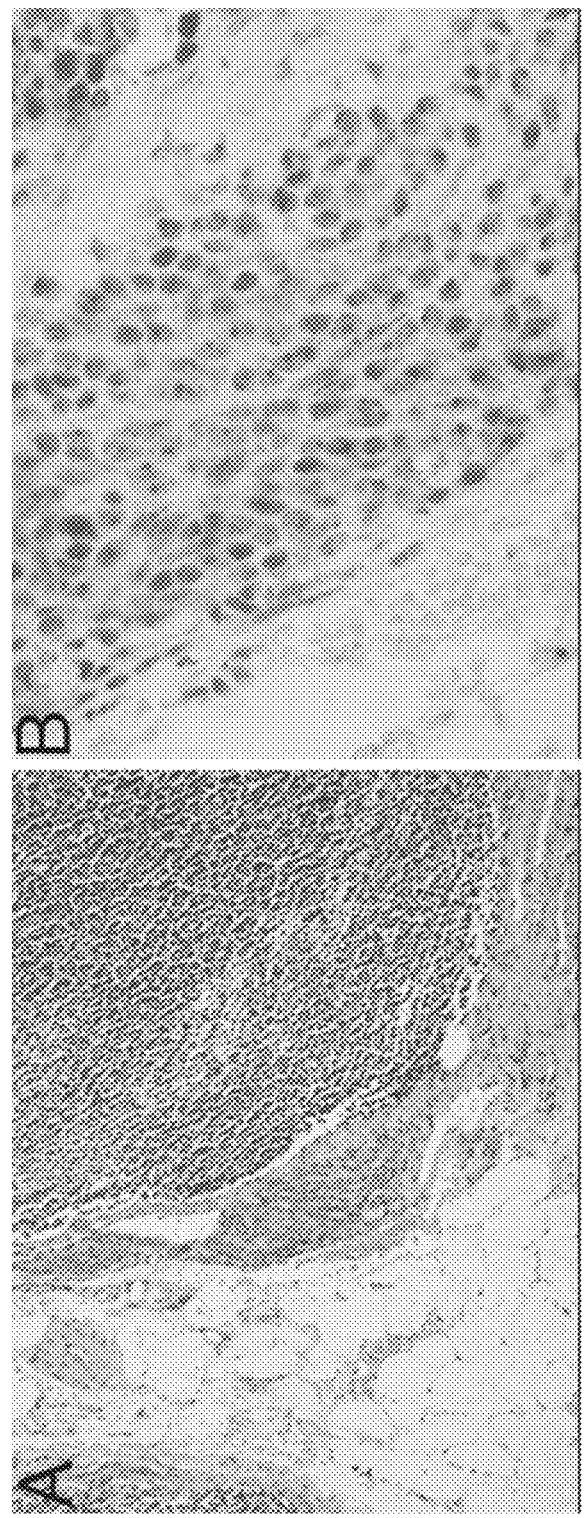
FIG. 26 is a photograph depicting a sAC staining pattern of sAC staining in benign capsular nevus. (A) Benign nevus cells are present within the lymph node capsule. (B) sAC Golgi staining is noted around the nucleus and there is incomplete granular nuclear staining. Pan-nuclear staining is not identified.

Histologic features: Collections of benign nevus cells within the lymph node capsule defines the concept of the benign capsular nevus.

sAC staining patterns: Benign capsular nevi show (i) weak diffuse cytoplasmic staining without any nuclear staining and/or (ii) dot-like Golgi staining. The sAC staining patterns of benign capsular nevi are not comparable to those observed in melanoma and/or other high-grade melanocytic proliferations (FIG. 26).

Atypical Nevus of Special Sites

Alternative nomenclature: An atypical nevus of special sites may also be referred to as an atypical nevus.

Figure 4:
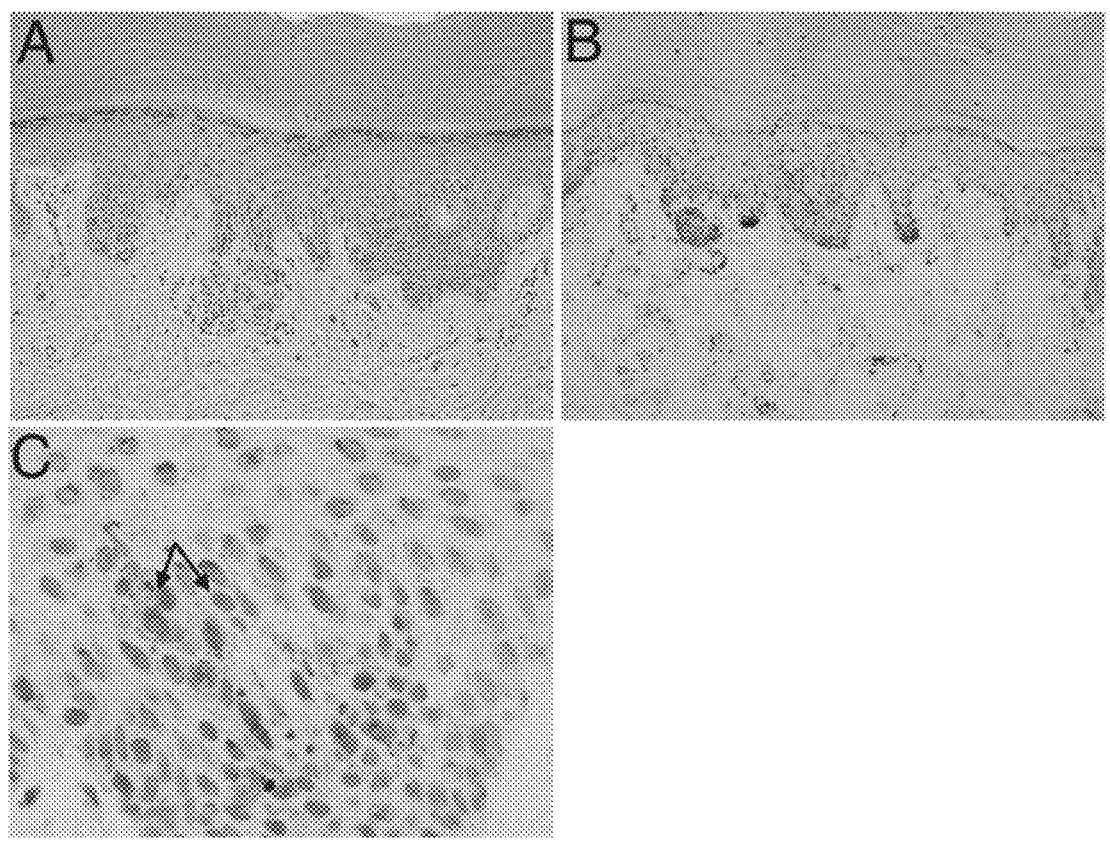
FIG. 4 is a photograph depicting a sAC staining pattern of an atypical nevus of special sites. (A) Nevi exhibiting low-grade atypia show a pattern similar to the benign nevus. Small foci of pagetoid ascent emanating from zones of junctional nested activity are observed. The lesion has relatively modest density without zones of confluent growth and the pagetoid foci define the minor component of the lesion. (B-C) In this mildly atypical nevus of special sites, a dot-like sAC staining pattern (arrow) is observed around the nucleus. Discernible nuclear staining is not seen.
Figure 5:
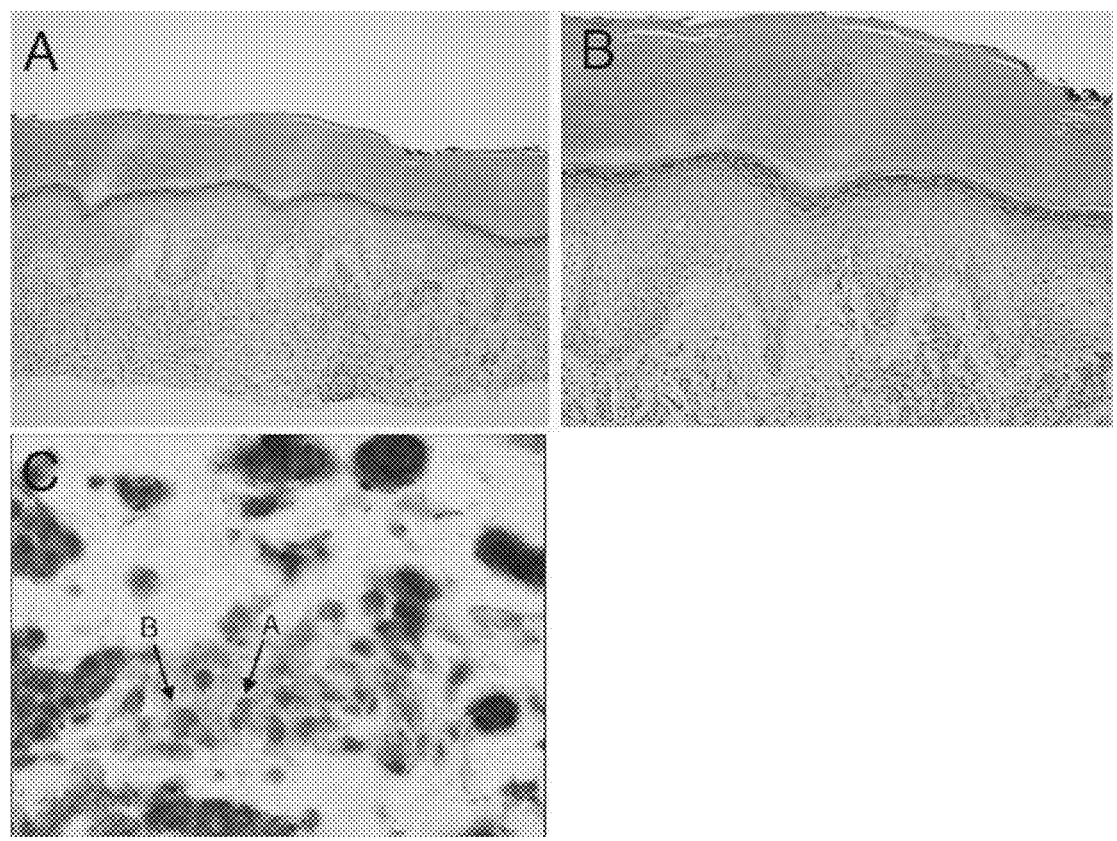
FIG. 5 is a photograph depicting a sAC staining pattern of an atypical nevus of special sites. (A-B) Pagetoid ascent is a cardinal hallmark of atypical nevi of special sites. In addition, there can be variable cytologic atypia. These lesions can sometimes be confused with malignant melanoma. (C) A dot-like sAC staining pattern (arrow A) and occasional broad Golgi staining (arrow B) are observed around the nucleus. Discernible nuclear staining is not seen.

Histologic features: Atypical nevi of special sites are not malignant, but may show atypical features suggestive of a dysplastic nevus or of a melanoma. The most important "special sites" include genital skin, acral skin, ear skin, and flexural skin. Some atypical nevi of acral sites have cytologic atypia and pagetoid spread of melanocytes through the epidermis that can make their morphologic distinction from melanoma difficult. Additionally, atypical nevi of acral sites can be precursors to melanomas of superficial spreading type and of acral lentiginous type.

sAC staining patterns: The sAC staining pattern of atypical nevi of special sites is similar to that of benign nevi, namely, a prominent dot-like perinuclear Golgi staining pattern (FIG. 4) with variable weak nucleolar staining. In cases exhibiting mild atypia, pan-nuclear staining is typically seen in less than 10% of intraepidermal melanocytes, and is often accompanied by weak nucleolar staining. No pan-nuclear staining is seen in dermal melanocytes. In cases exhibiting a higher grade of atypia, more intraepidermal melanocytes show pan-nuclear staining, while other melanocytes show intense incomplete granular nuclear staining. No pan-nuclear staining is seen in dermal melanocytes. Where pan-nuclear staining is not observed, there is generally preservation of the dot-like Golgi staining pattern in dermal melanocytes. In a particular case of an atypical nevus of flexural sites, no nuclear staining and broad perinuclear Golgi staining is observed (FIG. 5, arrow B).

Dysplastic Nevus

Alternative nomenclature: A dysplastic nevus may also be referred to as a nevus with architectural disorder and cytologic atypia or an atypical nevus.

Histologic features: Criteria that must be present for a diagnosis of dysplastic nevus are considered major criteria, and those additional criteria that are not present in every case, but, when observed, are further corroborative evidence of a diagnosis of dysplastic nevus, are considered minor criteria. A diagnosis of dysplastic nevus is made when both major and at least two minor criteria are met.

Major criteria include (1) asymmetric basilar proliferation of nevomelanocytes along the dermoepidermal junction extending laterally beyond the confines of a preexisting dermal component, if and when present, usually by three rete ridges or more and (2) characteristic cytomorphology, manifested as lentiginous melanocytic dysplasia or epithelioid cell melanocytic dysplasia.

Figure 7:
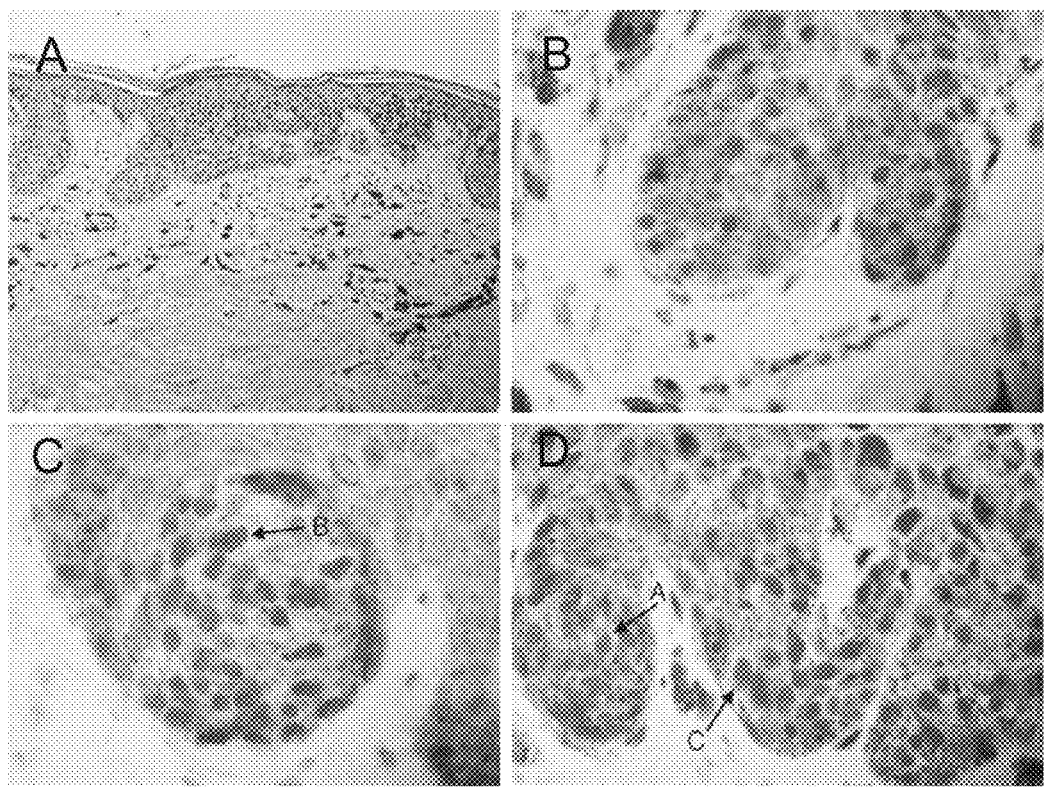
FIG. 7 is a photograph depicting a sAC staining pattern of a lentiginous compound dysplastic nevus with moderate atypia. (A) The compound melanocytic lesion exhibits characteristic hallmarks of a dysplastic nevus, including fusion of rete ridges by melanocytes and discernible moderate lentiginous dysplasia. Stromal changes of a dysplastic nevus are noted. (B-D) The sAC staining pattern is primarily in the context of a dot-like Golgi pattern (arrow A) with focal weak nucleolar staining (arrow B). There is also pan-nuclear staining manifested by a small percentage of the cells (arrow C).
Figure 8:
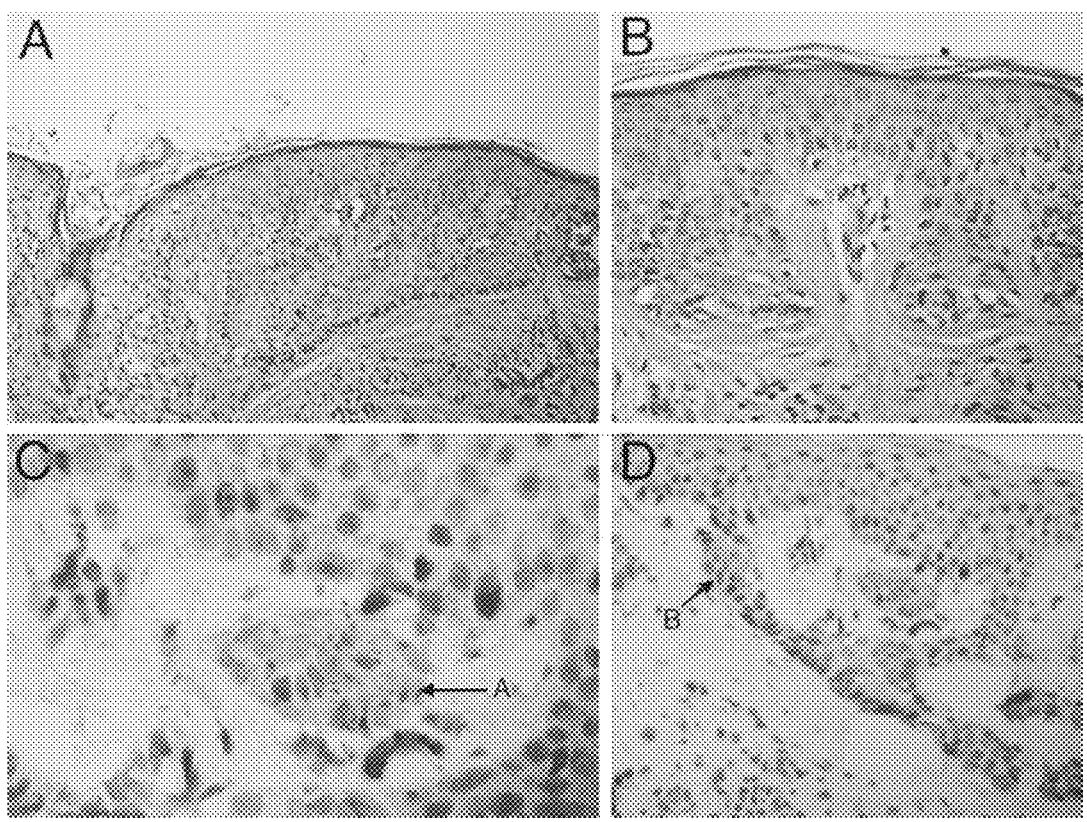
FIG. 8 is a photograph depicting a sAC staining pattern of a moderate to severely dysplastic nevus. (A-B) Significant melanocytic atypia is noted. The lesion was graded moderate to severely atypical based on the relatively confluent pattern of single cell lentiginous growth with supervening high grade lentiginous dysplasia. (C-D) In this example, the melanocyte sAC staining pattern is more complex. Perinuclear Golgi staining is noted, although not in every cell (arrow A). A number of cells show incomplete granular nuclear and nucleolar staining. Scattered cells exhibiting a pan-nuclear staining pattern are noted, although most of the cells are without pan-nuclear staining. Less than 25% of the cells show a pan-nuclear staining pattern (arrow B).

Minor criteria include (1) papillary dermal collagen with concentric eosinophilic fibrosis in which a dense zone of acellular brightly eosinophilic collagen envelops rete ridges and/or lamellar fibroplasia in which delicate layers of collagen are interspersed with spindle-shaped cells of presumptive neural crest origin, which function as facultative fibroblasts laying down collagen beneath the tips of hyperplastic retia in parallel arrays, (2) lymphocytic infiltrates in the papillary dermis, being of maximal intensity beneath areas in which melanocytes show cytologic atypia, (3) prominent vessels that may be newly formed or preexisting vessels that show endothelial cell activation and hyperplasia, and (4) fusion of retia by confluent growth between adjacent melanocytic nests.

sAC staining patterns: Dysplastic nevi with higher grades of atypia show greater pan-nuclear staining than those with lower grades of atypia. Irrespective of the extent of intraepidermal melanocytic atypia, the dermal component in dysplastic nevi lacks significant pan-nuclear staining. In almost all dysplastic nevi, a dominant perinuclear dot-like Golgi staining pattern is observed (FIG. 6, arrow A; FIG. 7, arrow A; FIG. 8, arrow A) in the majority of melanocytes in the epidermis and dermis. Nucleolar and focal granular nuclear staining can also be seen in a variable number of cells (FIG. 7, arrow B). A minor cell populace exhibits broad Golgi staining, especially in higher grade lesions.

Figure 6:
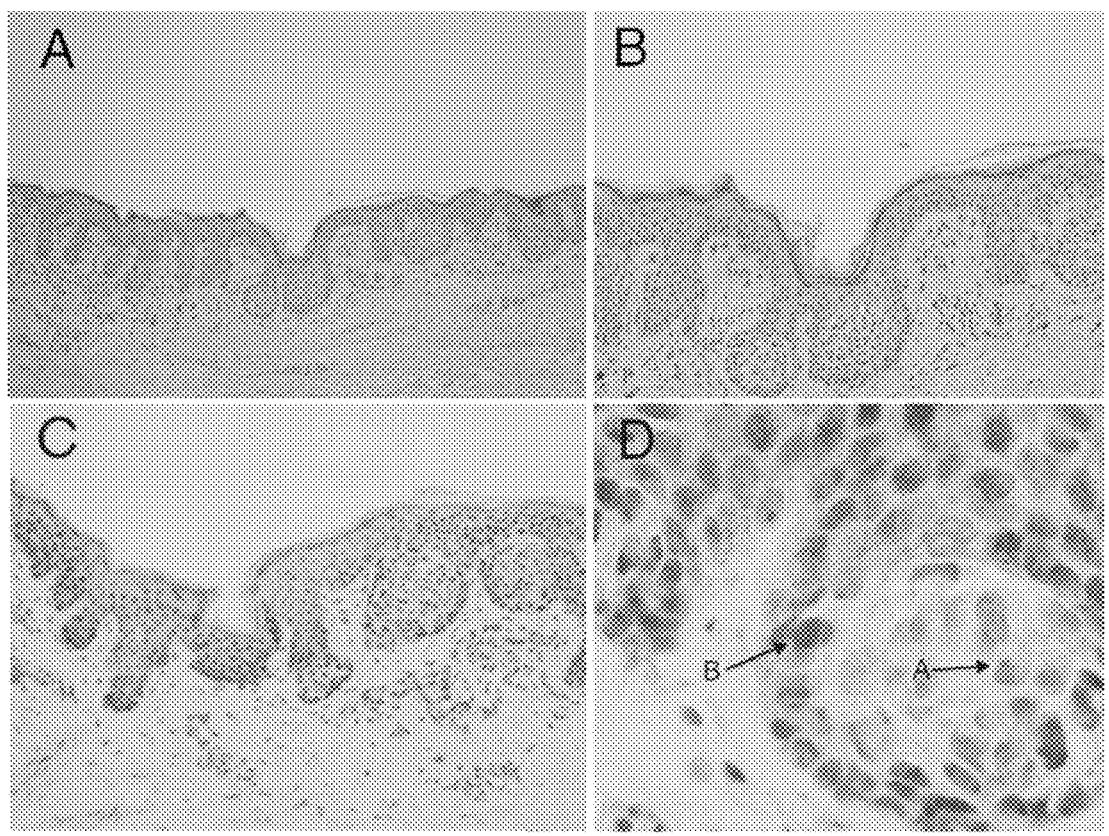
FIG. 6 is a photograph depicting a sAC staining pattern of a mildly dysplastic nevus. (A-B) The typical light microscopic findings of a compound dysplastic nevus are discernible, including an asymmetrical shoulder with nested melanocytes extending beyond the dermal based component. Slight cytologic and architectural atypia are discernable. (C-D) There is a dot-like sAC staining pattern around the nucleus typical of benign melanocytic lesions (arrow A). There is also a component of nuclear staining whereby the cells exhibit a weak nucleolar staining pattern along with incomplete granular nuclear staining (arrow B). Significant pan-nuclear staining is not seen.

Mildly dysplastic nevi, similar to benign nevi, are characterized by a dot-like Golgi staining pattern, in concert with a few lesional cells within the epidermis, typically less than 10%, having a pan-nuclear staining pattern (FIG. 6).

In higher-grade dysplastic nevi, many of the lesional melanocytes within the epidermis exhibit prominent nucleolar staining, with superimposed focal granular nuclear staining. A significant number of intraepidermal melanocytes, typically less than 25%, exhibit pan-nuclear staining (FIG. 6, arrow B; FIG. 7, arrow C; FIG. 8, arrow B).

Conventional Atypical Spitz Tumor

Alternative nomenclature: A conventional atypical Spitz tumor may also be referred to as a conventional atypical Spitz nevus, an atypical Spitz tumor of childhood, a conventional atypical Spitz tumor of childhood, a Spitz tumor, or a Spitz nevus.

Figure 19:
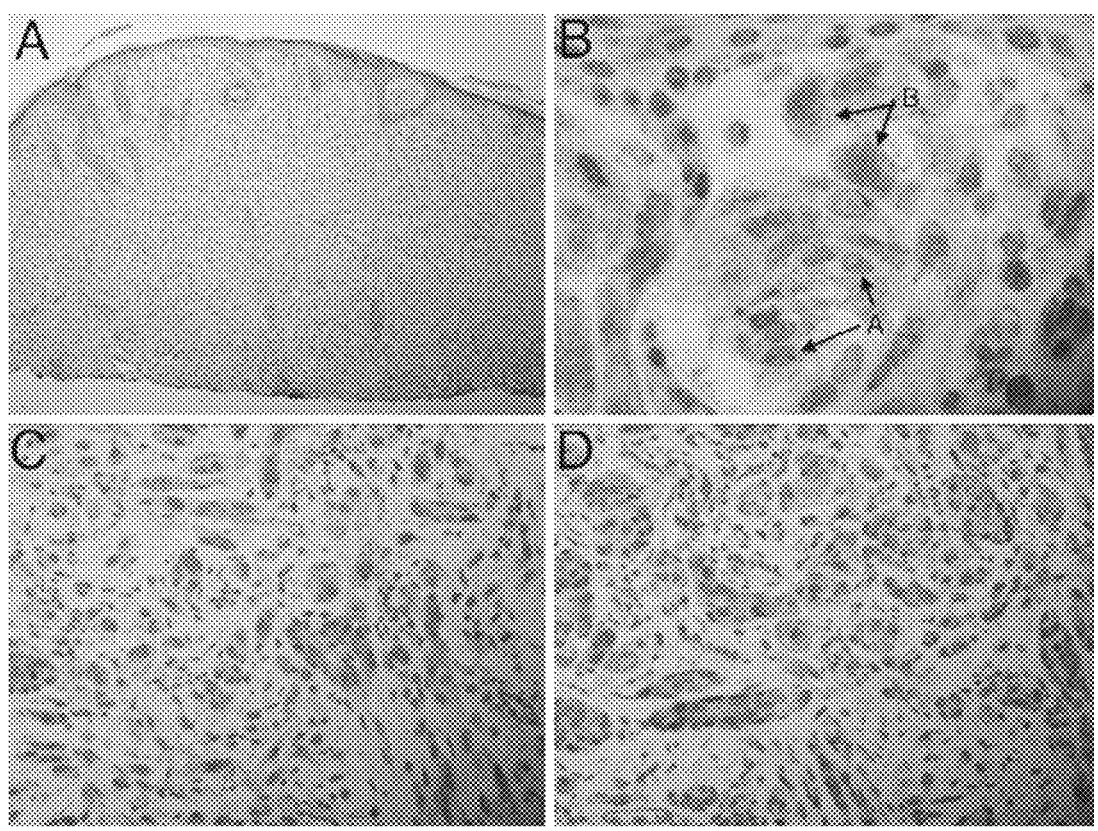
FIG. 19 is a photograph depicting a sAC staining pattern of a conventional atypical Spitz tumor, low risk variant. (A) There is a dermal based lesion characterized by cords and nests of somewhat large appearing epithelioid melanocytes with superficial mitotic activity. Architectural maturation is noted as revealed by a reduction in cell size and density as the base of the lesion is approached. (B-D) The sAC staining pattern is characterized by nucleolar prominence (arrow A) and a broad pattern of Golgi staining (arrow B). Noticeably absent is pan-nuclear staining and a discrete Golgi pattern of staining.
Figure 20:
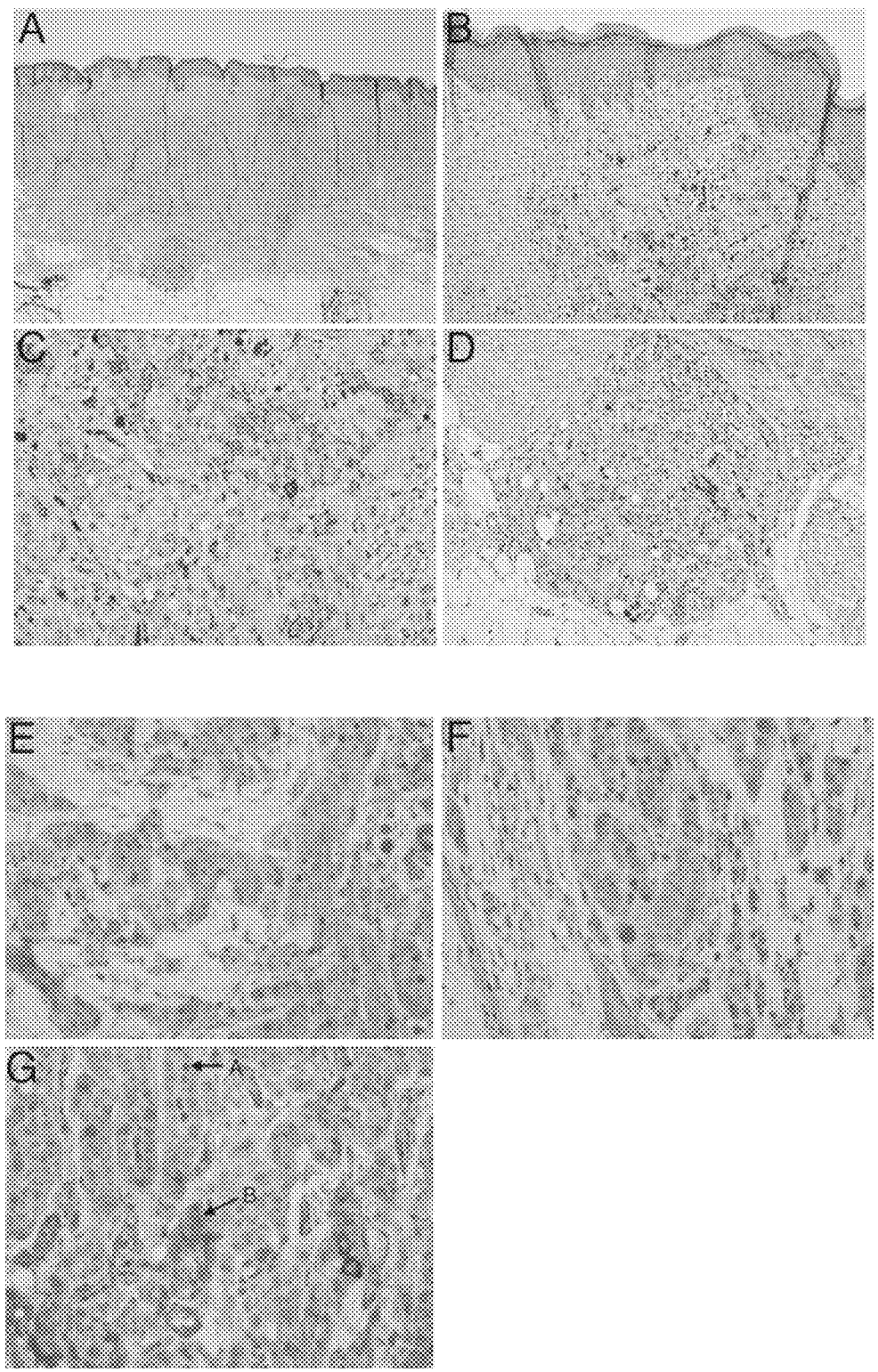
FIG. 20 is a photograph depicting a sAC staining pattern of a conventional atypical Spitz tumor, high-risk variant in an one year old. (A-D) There is severe cytologic atypia and no architectural maturation. The dominant growth pattern is nodular with extension into fat. The cells defining this lesion maintained a severely atypical large, epithelioid appearance throughout its depth. (E-G) Unlike the low risk variant, the sAC staining pattern is pan-nuclear (arrow A), albeit affecting only a minority of the dermal cells. While there is broad Golgi staining affecting roughly 10% of the cells, the more prominent pattern is one of diffuse cytoplasmic staining (arrow B). At variance with the staining pattern encountered in a conventional melanoma there is a relative lack of pan-nuclear staining. The absolute distinction in this case from a nodular melanoma is difficult. The pattern is strikingly different from the low-risk atypical Spitz tumor. The tumor was associated with positive regional lymph node disease.

Histologic features: The conventional atypical Spitz tumor manifests a sharply circumscribed dermal and epidermal nevomelanocytic proliferation, which assumes the architecture of an inverted cone with its base oriented parallel to the dermoepidermal junction and its apex pointing to-ward the subcutis. Characteristically, large theques of nevomelanocytes are present at the dermoepi-dermal junction, where they are separated by cleft-like spaces from the adjacent epidermis. Such nests are accompanied by hyperplasia of the epidermis, which may be pseudoepitheliomatous in character, with overlying hyperkeratosis and hypergranulosis. The papillary dermis appears edematous, and there is vascular ectasia. The junctional theques seem to "rain down" into the papillary dermis, as spindle cells orient themselves along elongated retia in a fashion perpendicular to the stratum corneum. The nests may manifest some dyshesion, a phenomenon that contrasts sharply with the adjacent intact epidermis. Eosinophilic hyaline bodies in the 30- to 40-micron size range, referred to as "Kamino bodies," may be seen in such nests and are present in 60% of all types of Spitz nevi. With respect to its cytological composition, the conventional atypical Spitz tumor typically comprises a variable admixture of epithelioid and spindled nevomelanocytes, the latter predominating in most examples.

sAC staining patterns: Lesions with low-risk features show prominent nucleolar staining (FIG. 19, arrow A) in concert with broad granular Golgi staining (FIG. 19, arrow B), but do not show significant pan-nuclear staining. Lesions with high-risk features additionally show diffuse cytoplasmic staining (FIG. 20, arrow B) and pan-nuclear staining in a minority of cells in both the dermis and epidermis (FIG. 20, arrow A).

Superficial Atypical Spitz Tumor

Alternative nomenclature: A superficial atypical Spitz tumor may also be referred to as a plaque type Spitz nevus.

Figure 21:
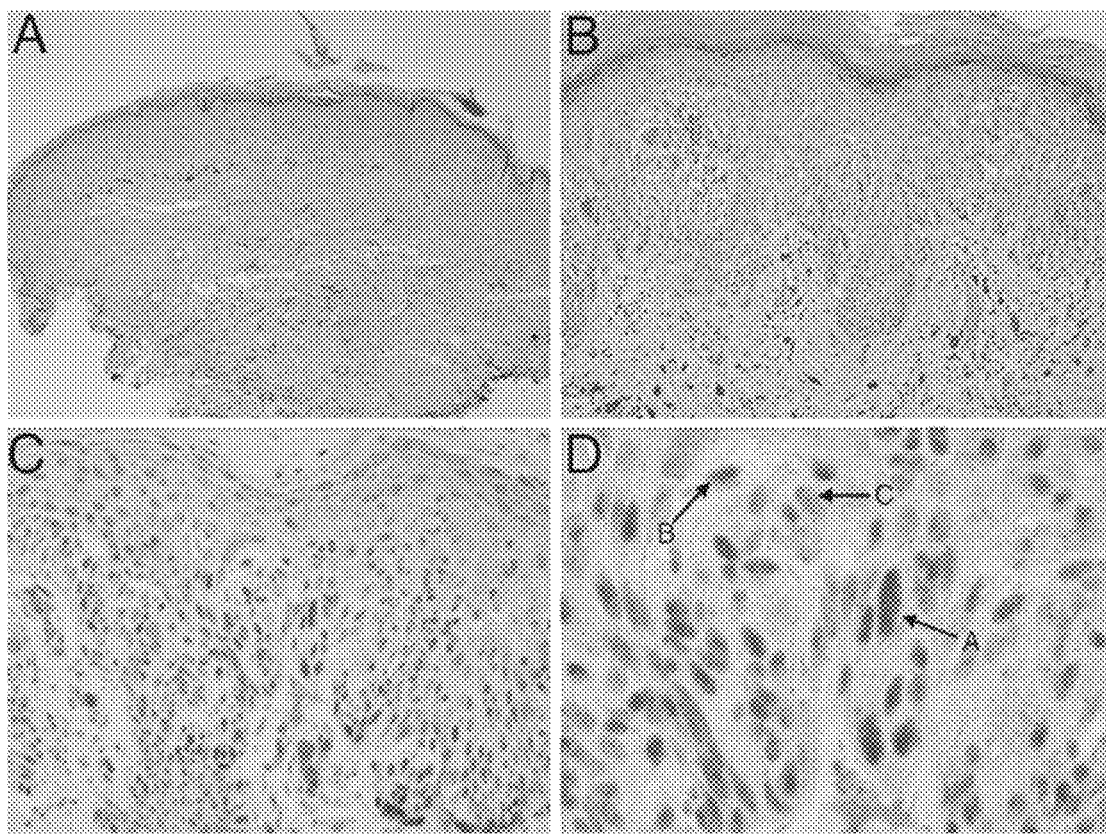
FIG. 21 is a photograph depicting a sAC staining pattern of a superficial atypical Spitz tumor with severe atypia. (A-B). There is a superficial compound melanocytic proliferation associated with significant pagetoid ascent. Although the cells demonstrate a spindled and epithelioid Spitzoid-like morphology, there is supervening dysplasia. (C-D) The sAC staining pattern shows a weak, broad Golgi pattern (not depicted). A significant number of cells demonstrate pan-nuclear staining (arrow A), while other cells show incomplete granular nuclear (arrow B) and conspicuous nucleolar staining (arrow C). The case was graded severely atypical.
Figure 22:
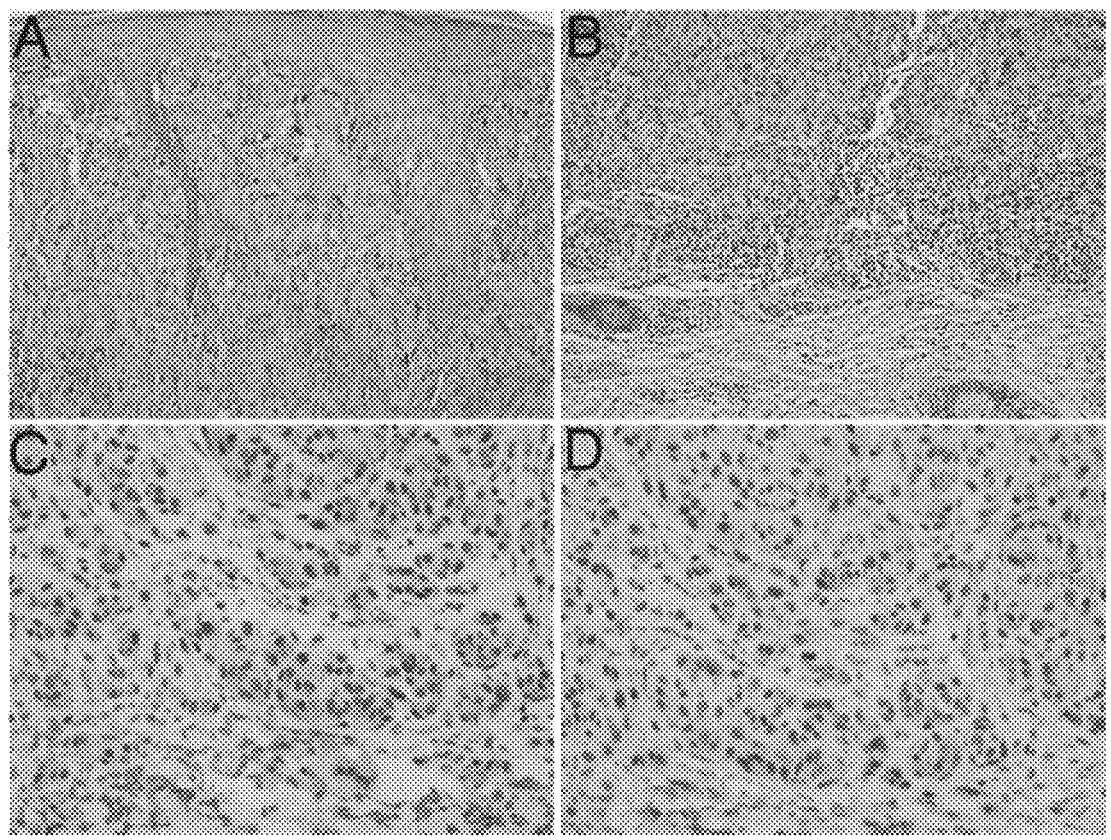
FIG. 22 is a photograph depicting a sAC staining pattern of a nodular melanoma with Spitzoid features arising in an 8 year old. (A-B) The excision specimen was remarkable for a highly atypical epithelioid tumor contiguous with the epidermis. There was no evidence of cytomorphologic and/or architectural maturation. (C-D) The sAC staining pattern is reminiscent of a nodular melanoma with extensive pan-nuclear staining, no apparent Golgi staining, and diffuse cytoplasmic staining.

Histologic features: Biopsy specimens are represented by relatively superficial compound melanocytic proliferations. In the majority of cases, the dermal component is largely confined to the papillary dermis (i.e., Clark level III equivalent). The epidermis ranges in quality from being hyperplastic to areas of epithelial thinning. Pagetoid spread is seen and can define the dominant growth at the lateral borders of the lesion. Lesions are defined by Spitzoid-appearing epithelioid and spindle cells. Pleomorphic ganglion-like cells are seen in some cases and are located predominantly within the dermis. Most cases show features of dysplasia amidst the defining intraepidermal- and dermal-based cell populations of varying degrees based on the presence of considerable cell size and shape heterogeneity, nuclear contour aberrations, and conspicuous nucleolation particularly amidst epithelioid cells. In some cases the atypia is severe and is accompanied by enhanced architectural atypia. In some cases, the lesions exhibit characteristic architectural changes that one associates with a dysplastic nevus, including rete ridge elongation and fusion along with drapelike fibroplasia. A dermal component is observed in the majority of cases whereby the cells typically assume a single cell and/or small nested growth pattern without any zones of dermal effacement. Dermal mitoses are not identified apart from occasional junctional mitoses. A characteristic feature seen in some cases is a plaque-like expansion of the dermis by sclerotic collagen. The sclerosis is somewhat reminiscent of regression, however, the stroma is more hyalinized and contains randomly disposed hallmark Spitzoid multinucleated cells.

sAC staining patterns: Superficial atypical Spitz tumors show broad Golgi staining with prominent nucleolar staining (FIG. 21, arrow C) in most cases, and dot-like Golgi staining in a minority of cases. A minority of cells in the dermis show pan-nuclear staining. Pan-nuclear staining of cells in the epidermis (FIG. 21, arrow A) is variable, and can be extensive, mimicking melanoma, in cases with severe cytologic atypia. In contradistinction, in a particular case of an 8 year old with nodular melanoma with Spitzoid features, there is no nucleolar staining, despite significant pan-nuclear staining; the cytoplasm is diffusely positive (FIG. 22).

Borderline Deep Penetrating Nevus-like Lesion

Alternative nomenclature: A borderline deep penetrating nevus-like lesion may also be referred to as a borderline melanocytic lesion arising in association with a deep penetrating nevus or a borderline melanocytic lesion with deep penetrating nevus-like features.

Figure 23:
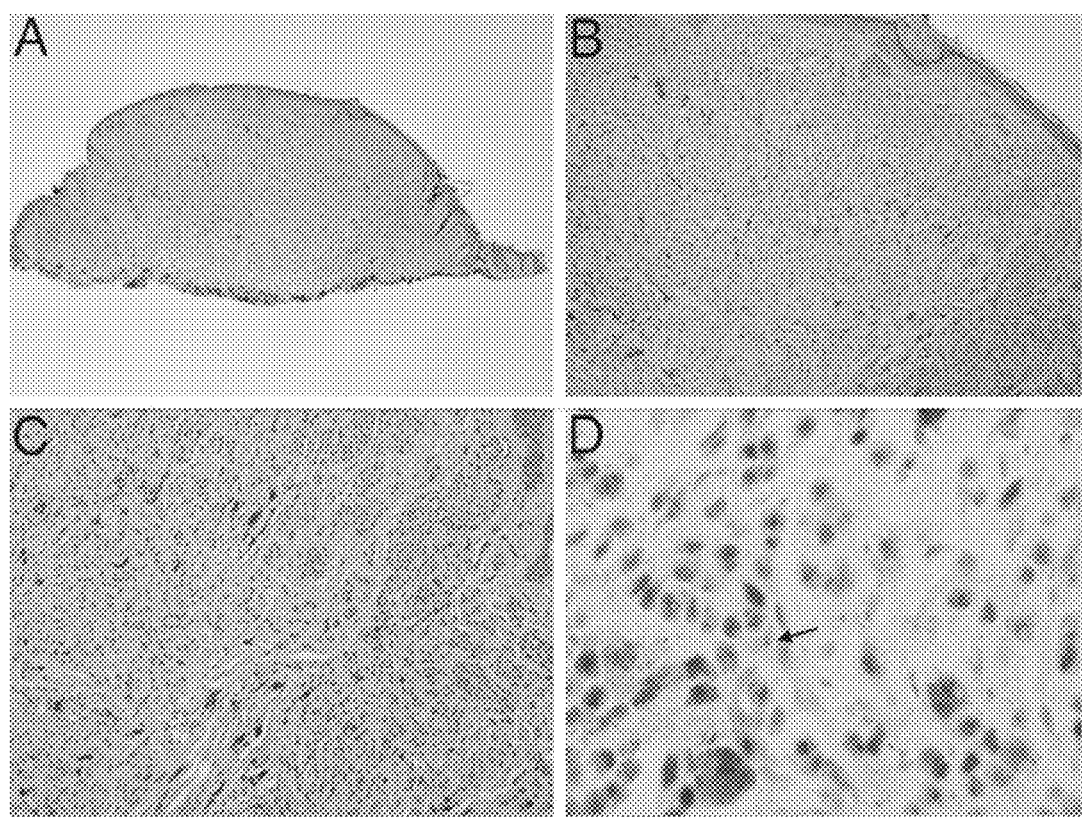
FIG. 23 is a photograph depicting a sAC staining pattern of a low-risk borderline tumor with deep penetrating nevus-like features. (A-C) The lesion is defined by a proliferation of spindle and epithelioid melanocytes disposed in nests and fasciles, which focally assume a somewhat perpendicular orientation to the long axis of the epidermis. The cells have fairly abundant cytoplasm and exhibit variable melanization. The categorization as a borderline tumor is based primarily on the cellularity of the growth pattern noted more superficially. (D) The sAC staining pattern shows minimal pan-nuclear staining. Many of the melanocytes show incomplete granular nuclear and nucleolar staining. The Golgi pattern is not well visualized in this image, but has a predominantly peri-nuclear dot-like pattern (arrow).
Figure 24:
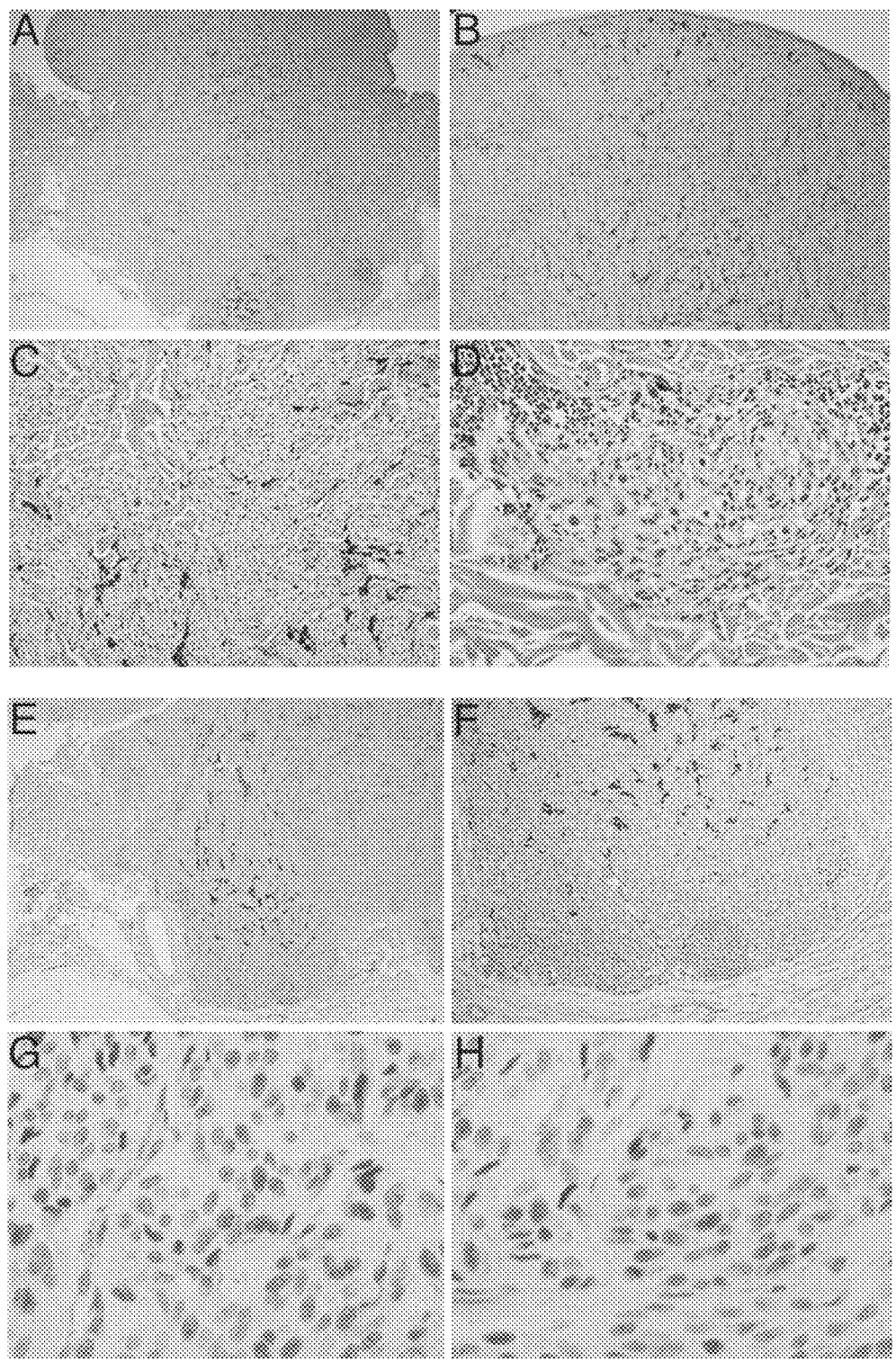
FIG. 24 is a photograph depicting a sAC staining pattern of a high-risk borderline tumor with deep penetrating nevus-like features. (A-F) High-risk features are identified including the extensive pan dermal nodular growth pattern with zones of effacing dermal growth. There is cytologic atypia although overt features of malignancy are not seen. The lesion maintains a deep penetrating nevus-like appearance based on the epithelioid cytomorphologic composition along with the plexiform growth pattern with accentuation of lobulated growth around adnexal structures. (G, H) The sAC staining pattern shows a number of cells exhibiting a pan-nuclear pattern. There is a noticeable loss of the Golgi pattern.

Histologic features: Borderline deep penetrating nevus-like lesions exhibit all of the typical features of a deep penetrating nevus (DPN) along with additional features not encountered in the classic DPN. In particular, there is supervening cellular proliferative areas arranged to the long axis of the epidermis, in contradistinction to the dominant orderly vertical orientation seen in the typical DPN, or a nodular expansile growth at the base. An expansile nodular growth pattern in the zones of vertically oriented melanocytic proliferation is also seen. Such foci also manifest enhanced cytologic atypia with cellular enlargement and increased mitotic activity, including marginal mitoses. Unlike the other subcategories of borderline melanocytic tumors, the abnormal proliferative foci can be superficially confined albeit still located in the reticular dermis, while the deeper aspect of the neoplasm can be within the spectrum of residual DPN.

sAC staining patterns: In borderline deep penetrating nevus-like lesions, the number of cells demonstrating pan-nuclear staining varies with the extent of cytologic and architectural atypia. Low risk lesions show both dot-like and broad Golgi staining, nucleolar and incomplete granular staining in a majority of cells, and pan-nuclear staining in a minority of cells. One case of a low-risk lesion shows preserved dot-like Golgi staining (FIG. 23, arrow) with minimal pan-nuclear staining. High-risk lesions show significant pan-nuclear staining in addition to loss of dot-like Golgi staining (FIG. 24), acquisition of broad Golgi staining, and/or diffuse cytoplasmic staining.

Nevoid Borderline Tumor

Alternative nomenclature: A nevoid borderline tumor may also be referred to as a minimal deviation melanoma or a melanocytic tumor of undetermined malignant potential (MELTUMP).

Figure 25:
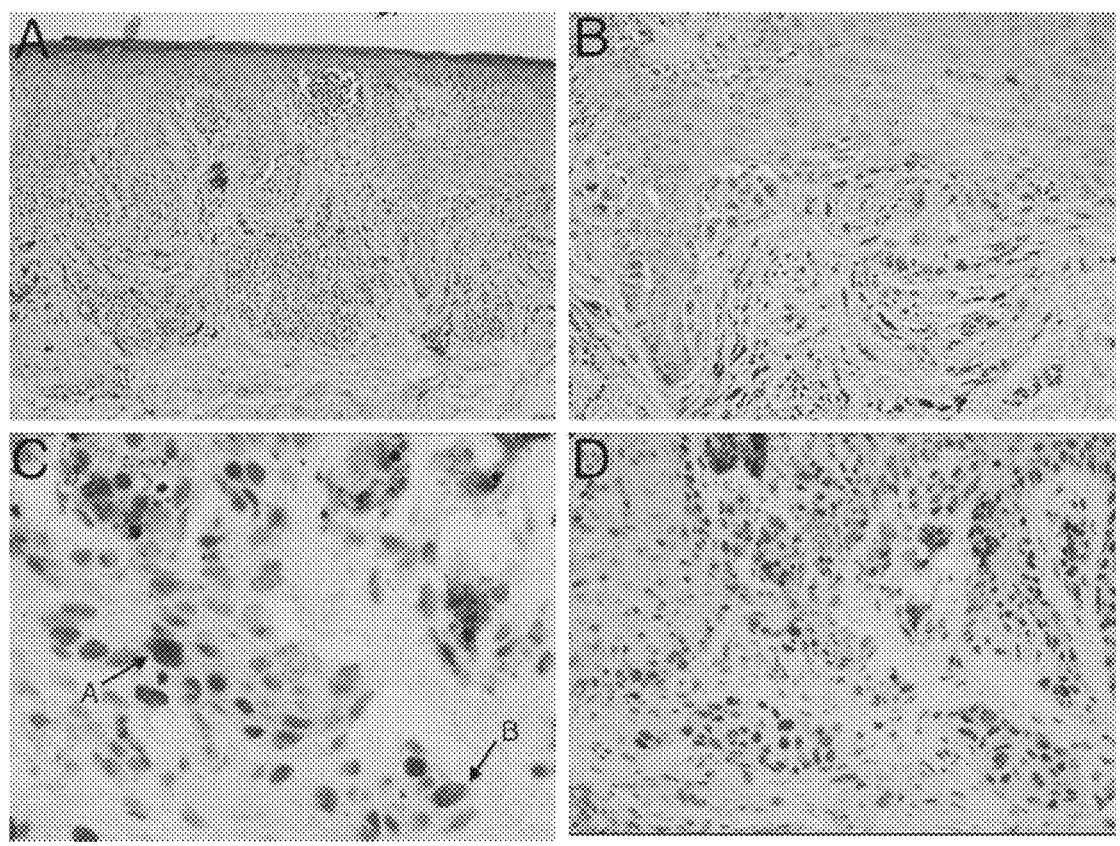
FIG. 25 is a photograph depicting a sAC staining pattern of a nevoid borderline tumor. (A-B) There is significant intraepidermal and dermal melanocytic atypia with focal pagetoid ascent, along with background stromal changes of a dysplastic nevus. The cytologic atypia is characterized by significant cellular enlargement with nuclear hyperchromasia. The defining cells, while atypical, are not diagnostic of melanoma. The differential diagnosis of this lesion is a severely atypical borderline tumor versus frank melanoma. (C, D) The sAC staining pattern shows significant intraepidermal and dermal pan-nuclear staining, although not in excess of 30% of the cells (arrow A). Several of the cells exhibit conspicuous nucleolar and incomplete granular nuclear staining (arrow B). Overall, the light microscopic appearance of the lesion along with the sAC profile is consistent with a severely atypical lesion, albeit not one representing melanoma.

Histologic features: The low-power architecture is a nested proliferation with sharp lateral circumscription. At variance with the symmetrical silhouette of a compound or dermal nevus is the expansile quality of the dermis-based nests. In some cases, the intraepidermal component may be absent, while in the other cases a narrow grenz zone of uninvolved papillary dermis separates dermal nests from areas of intraepidermal melanocytes. The nests situated in the mid and deeper dermis are larger than the more superficial nests. Occasional mid-dermal mitoses are observed. The cells are cytologically atypical, but do not show features diagnostic of fully evolved melanoma. An element of monotypism defines the cell population and is at variance with the classic nevus, which shows maturation with dermal descent, specifically from a type A nevomelanocyte to a spindled type C nevus cell. Cells are noticeably smaller than those cells of nevoid melanoma, but differ from the classic melanocytic nevus by a cell size that is larger at the base compared to the cells seen in the deep aspect of a benign melanocytic nevus; there are cells at the base, the size of which exceed that of cells located more superficially. Dispersed throughout the lesion, especially at the base, are cells demonstrating conspicuous nucleoli, nuclear grooves, and increased nuclear to cytoplasmic ratios, although such cells do not define the dominant population. Lesional cells in all cases extend into the reticular dermis.

sAC staining patterns: There are two main categories of nevoid borderline tumors. One main category of nevoid borderline tumors is characterized by a superficial dermal/epidermal melanocytic proliferation with significant atypia that simulates superficially invasive melanoma of superficial spreading type. These cases show extensive pan-nuclear staining, with more atypical cases showing patterns approaching those seen in melanomas. However, pan-nuclear staining in the dermis is less extensive than in melanoma. As in superficial spreading melanomas, the Golgi staining pattern is either absent or broad. A variable number of cells with preserved dot-like Golgi staining can be seen. In dermal nevoid borderline tumors, which is the second main category of nevoid borderline tumors, lesions resemble a dermal nevus with supervening melanocytic atypia that can be moderate or severe; distinction from melanoma is revealed by the dominant dot-like Golgi staining in most cases, albeit accompanied by some degree of broad Golgi staining. There is pan-nuclear staining, but in fewer cells than in melanoma (FIG. 25).

Lentigo Maligna Melanoma

Histologic features: The characteristic histomorphologic appearance of lentigo maligna, which is the precursor to lentigo maligna melanoma, is one of polygonally shaped melanocytes with hyperchromatic, angulated nuclei dispersed as individual units, initially confined to the basal layer of epidermis in a discontiguous lentiginous fashion. These abnormal cells extend along the eccrine ducts and the outer root sheath epithelium of hair follicles, permeating the mid- and lower portions of the isthmus and below. Another characteristic feature of the cytomorphology of lentigo maligna is the multinucleated giant melanocyte along the basal layer of the epidermis. Termed "star-burst giant cells," these may contain more than 30 nuclei and have been identified in up to 85% of all cases of lentigo maligna. The epidermis in lentigo maligna is characteristically atrophic, manifesting thinning and loss of the retiform pattern overlying elastotic dermal collagen; telangiectasia and melanophages complete the early picture which has been designated as a precursor to melanoma. As the lesion progresses clinically and histologically, continuity of single-cell basilar melanocytic proliferation is observed, followed by a nested pattern of junctional activity. Specifically, variably sized dyshesive junctional theques form along the dermo-epidermal junction; such nests assume a parallel disposition to the long axis of the epidermis. This distinctive nest morphology has been referred to as "the swallow's nest sign." In addition, foci of prominent pagetoid infiltration are observed with lesional progression. Nesting, confluence of melanocytes along the basal layer and pagetoid spread of neoplastic melanocytes, which are considered to represent the features of melanoma in situ, are the harbingers of the next phase of lesional evolution, namely, dermal invasion.

Figure 11:
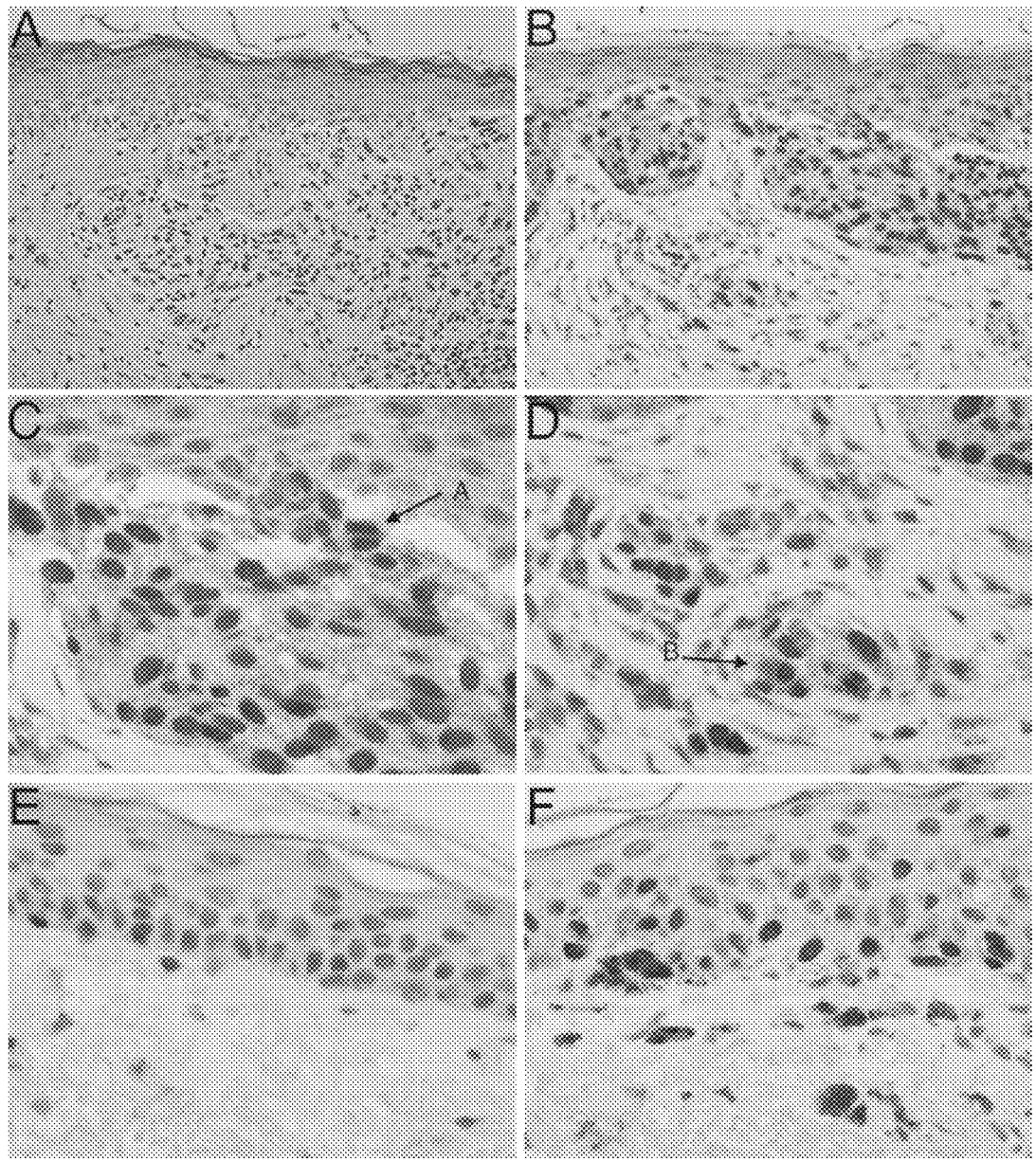
FIG. 11 is a photograph depicting a sAC staining pattern of a lentigo maligna melanoma. (A) The biopsy shows a confluent single cell and nested proliferation of severely atypical melanocytes along the dermal epidermal junction. The cells exhibit classic lentiginous dysplasia, as defined by striking nuclear hyperchromasia, nuclear angulation, and an overall increase in cell size. (B-D) sAC staining demonstrates extensive pan-nuclear staining of melanocytes within the epidermis and dermis (arrow A). A broad Golgi pattern is seen (arrow B). (E) Only benign photoactivated melanocytes exhibiting a Golgi pattern are noted at the lateral margin. (F) In contrast, striking pan-nuclear staining of malignant melanocytes is present at an inked margin of resection.
Figure 12:
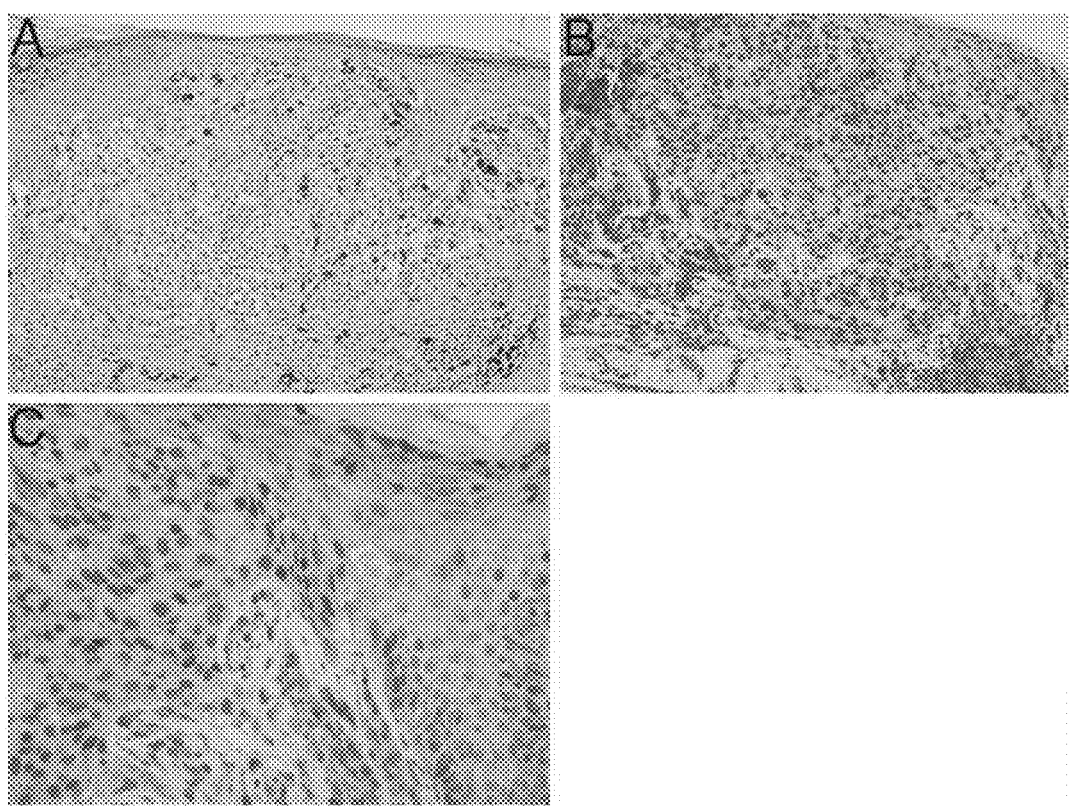
FIG. 12 is a photograph depicting a sAC staining pattern of a superficial spreading melanoma. (A) The intraepidermal melanocytic proliferation has severely atypical epithelioid-appearing melanocytes. The lesion is of high density and associated with epideinial effacement. (B-C) The sAC staining pattern is very abnormal showing pan-nuclear staining pattern with minimal Golgi staining.

Pagetoid spread is unusual in early lesions. When pagetoid spread occurs, the cytomorphology is characteristically that of an epithelioid cell type similar to that observed in lesions of de novo intraepidermal epithelioid melanocytic dysplasia and malignant melanoma in situ of superficial spreading type. A prominent nested pattern and areas of conspicuous pagetoid infiltration usually signify a high risk that progression to microinvasive radial growth phase-confined melanoma has occurred. Other clues to the evolution from in situ melanoma to microinvasive melanoma is the presence of a lichenoid infiltrate with admixed melanophages in a papillary dermis that exhibits laminated sclerosis. Such findings warrant careful scrutiny of the inflamed papillary dermis for singly disposed neoplastic melanocytes. In the event that unequivocal invasive malignant melanoma is not identified, the presence of regressive stromal changes and an inflammatory host response indicates that an antecedent microinvasive component cannot be excluded. Neovascularization also may be a feature. The microinvasive cells are usually singly disposed and have a cytomorphology virtually identical to those cells within the epidermis that are interpreted as representing melanoma in situ. Typically they have an epithelioid morphology, usually manifesting fairly abundant, variably pigmented cytoplasms.

sAC staining patterns: In lentigo maligna melanomas, most cases show prominent pan-nuclear homogeneous and/or granular staining in the majority of neoplastic melanocytes (FIG. 11, arrow A). Golgi staining may be absent, but where Golgi staining is discernible, it is typically of the broad staining pattern (FIG. 11, arrow B). No discernible diffuse cytoplasmic staining is observed. The prominent pan-nuclear staining allows for easy discrimination between lentigo maligna and background changes of chronic photoactivation (FIGS. 11E and 11F).

Acral Lentiginous Melanoma

Histologic features: Acral lentiginous malignant melanoma occurs predominantly on the palms, soles, subungual regions, and digits and is the most common type of malignant melanoma. The incipient lesion of acral lentiginous melanoma manifests as atypical melanocytes dispersed singly in a lentiginous array with foci of confluent basilar growth. There may be hyperplasia of the epidermis alternating with zones of epidermal effacement, and an overlying dense orthohyperkeratotic scale may be observed. Transepithelial pigment elimination is characteristic and assumes a haphazard pattern, unlike the organized pigment columns associated with benign acral nevi. Almost invariably, a mononuclear cell inflammatory response is present in the superficial dermis, a finding that is uniformly lacking in common acquired acral nevi. The infiltrate can assume a lichenoid pattern with resultant foci of subepidermal cleft formation. With further progression of the radial growth phase, pagetoid infiltration of the epidermis may come to comprise the dominant pattern of intraepidermal growth. The cytomorphology of the lentiginous component is one of large cells with hyperchromatic angulated large cells and scant cytoplasm; nuclear detail is obscured. Prominent dendritic processes from lentiginously-disposed neoplastic-melanocytes may extend into the upper layers of the stratum spinosum. When in a pagetoid array, the neoplastic melanocytes typically have an epithelioid morphology. Such lesions can mimic superficial spreading malignant melanoma, which can also be seen in acral sites. They extend randomly into the epidermis independent of the nested junctional component. Tropism to adnexal structures may be prominent. A single-cell pattern typically predominates over a nested pattern, whereas the converse is true in benign nevi. The nests are variable in size and shape, manifest dyshesion, and are composed of cells with either an epithelioid or spindled morphology. Although large and variably sized and disposed nests may be seen in the prototypic benign acral nevus, the cells of acral melanoma show severe nuclear atypia and the single-cell pattern of growth is dominant and predominant, a feature that is not at all typical of the prototypic acral melanocytic nevus.

Figure 9:
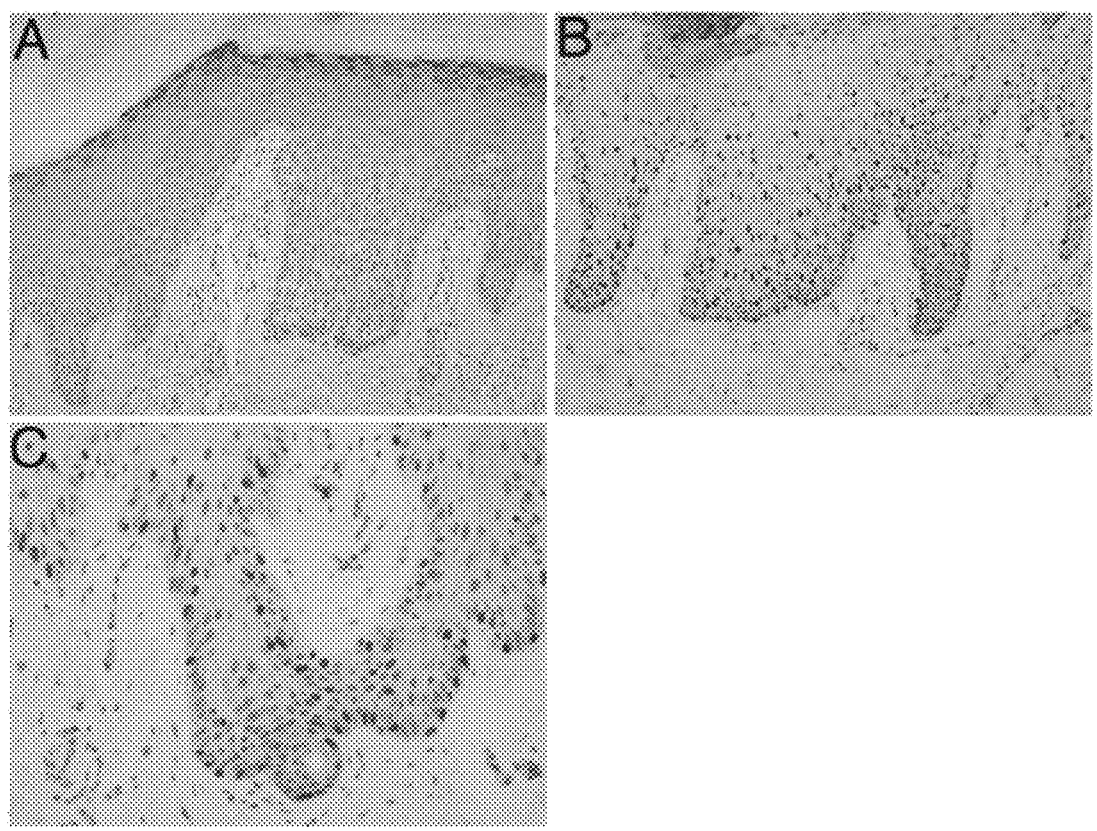
FIG. 9 is a photograph depicting a sAC staining pattern of an acral lentiginous melanoma. (A) The biopsy shows a high density lentiginous and pagetoid growth of severely atypical melanocytes. (B-C) sAC staining demonstrates extensive pan-nuclear staining of melanocytes within the epidermis, highlighting the atypical melanocytes in a lentiginous and pagetoid array. Discernible Golgi staining is not apparent.
Figure 10:
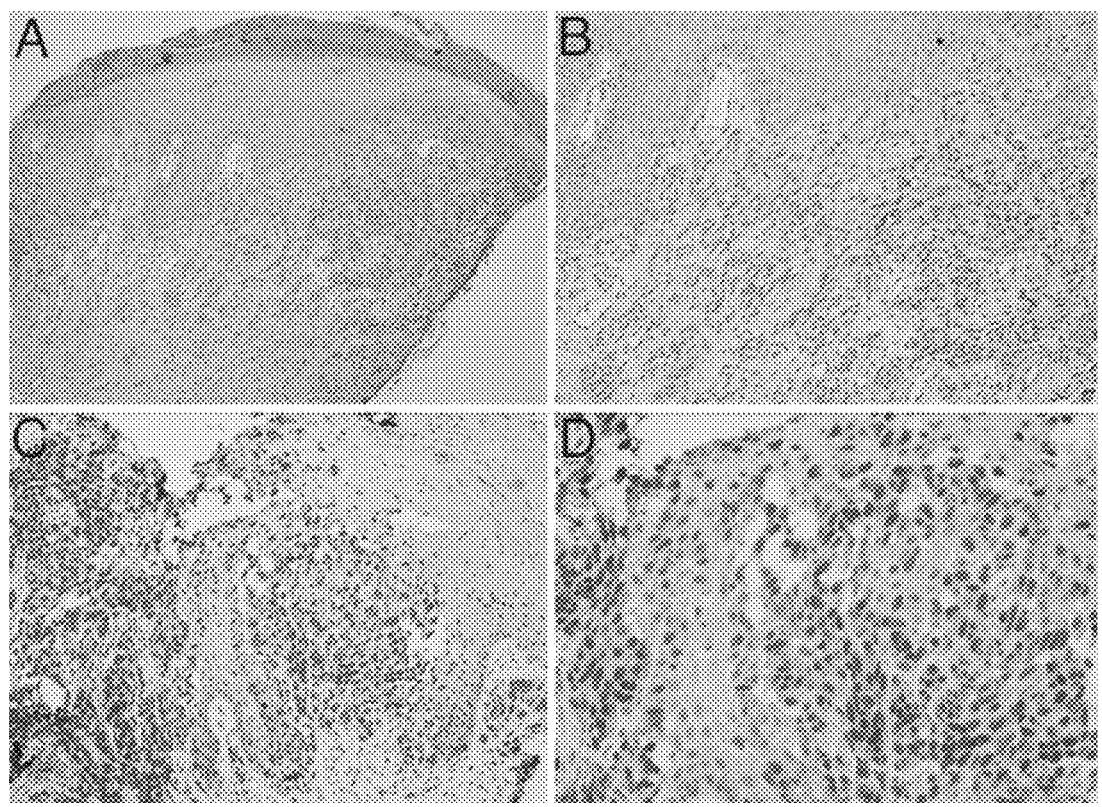
FIG. 10 is a photograph depicting a sAC staining pattern of an acral lentiginous melanoma. (A-B) The biopsy specimen shows a markedly atypical compound melanocytic tumor associated with a confluent, high-density growth of melanocytes along the dermal epidermal junction with foci of pagetoid ascent. The subjacent dermis exhibits a malignant spindled infiltrate. (C-D) sAC staining demonstrates extensive pan-nuclear staining of melanocytes within the epidermis and dermis; virtually all of the cells exhibit this pattern of pan-nuclear staining. Discernible Golgi staining is not apparent.

The invasive component of radial growth phase acral lentiginous melanoma comprises cells in a single-cell or nested disposition with a cytomorphology similar to those cells within the epidermis. The invasive single cells usually exhibit more abundant cytoplasms, often with fine pigmentation. Mitoses are common in the intraepidermal component. Dominant dermal nests manifesting mitoses are not present in the radial growth phase of malignant melanoma at any site; their presence signifies progression to vertical growth phase melanoma. A precursor lesion, although uncommon, has been reported.

sAC staining patterns: In most cases of acral lentiginous melanomas, neoplastic melanocytes demonstrate a distinctive pattern of lentiginous dysplasia characterized by enlarged cells with darkly staining angulated nuclei representing the large majority of intraepidermal melanocytes (FIGS. 9-10). These cells exhibit intense broad Golgi staining. The majority of cells also show pan-nuclear staining (FIGS. 9-10) and no discernible diffuse cytoplasmic staining.

Superficial Spreading Melanoma

Histologic features: By definition, superficial spreading malignant melanoma must have a radial growth phase. In its inception, this radial growth phase is confined to the epidermal compartment.

One intraepidermal growth pattern manifests an epithelioid cytomorphology and pagetoid architecture. Specifically, the cells have round-to-oval nuclei with thick nuclear chromatinic rims, macronucleoli, and abundant quantities of eosinophilic to amphophilic cytoplasm within which variably sized and shaped melanin granules are identified. These cells grow in a haphazard (pagetoid) fashion with single-cell dispersal through the epidermis to the cornified layer. Scattered mitotic figures may be seen. The epidermis is frequently hyperplastic.

A second intraepidermal growth pattern is one of a contiguous lentiginous proliferation of singly disposed cells along the dermo-epidermal junction. There is retiform effacement. Because of the confluent lentiginous melanocytic growth, discernible basilar keratinocytes are not observed. The cytologic character of the atypical cells that comprise this lentiginous pattern is one of angulated, hyper-chromatic nuclei that may lack internal nuclear detail and exceed the size of adjacent keratinocyte nuclei. The cytoplasm of each cell is ample and contains finely dispersed melanin granules.

A third intraepidermal growth pattern is one of confluent oblong nests composed of hyperchromatic spindle-shaped cells with distinct nuclear grooves, prominent nuclear chromatinic rims, eosinophilic nucleoli, and variable melanization. The deposition of pigment is irregular. There may be retiform effacement. In many cases, a hybrid pattern of intraepidermal growth is observed with a combination of the aforesaid patterns of architectural disposition and cytomorphology.

Lymphocytic infiltration is frequently observed in the subjacent papillary dermis and may herald the onset of incipient microinvasive malignant melanoma. Delicate fibroplasia is commonly seen. The organized periretal stromal response of the dysplastic nevus is not observed in such areas, however, unless it is seen in the context of a residuum of a precursor dysplastic nevus at the site.

The next phase in the progression of radial growth phase malignant melanoma is the development of microinvasive tumor confined to the papillary dermis. This component comprises both nested and dispersed single cells with a cytomorphology similar to the intraepidermal cells. However, the singly disposed invasive melanoma cell frequently exhibits more abundant cytoplasm with an eosinophilic hue. The nests should not exceed the size of any nest along the dermo-epidermal junction, nor should dermal-based mitoses be identified; either of these features suggests incipient vertical growth phase melanoma. In a small minority of superficial spreading malignant melanomas, the radial growth phase comprises spindled melanocytes. As mentioned, radial growth phase-confined malignant melanoma may arise in a background of a dysplastic nevus. Usually the foci of residual dysplastic nevus are present at the periphery. However, at times they present as small foci interposed between areas of melanoma.

Figure 14:
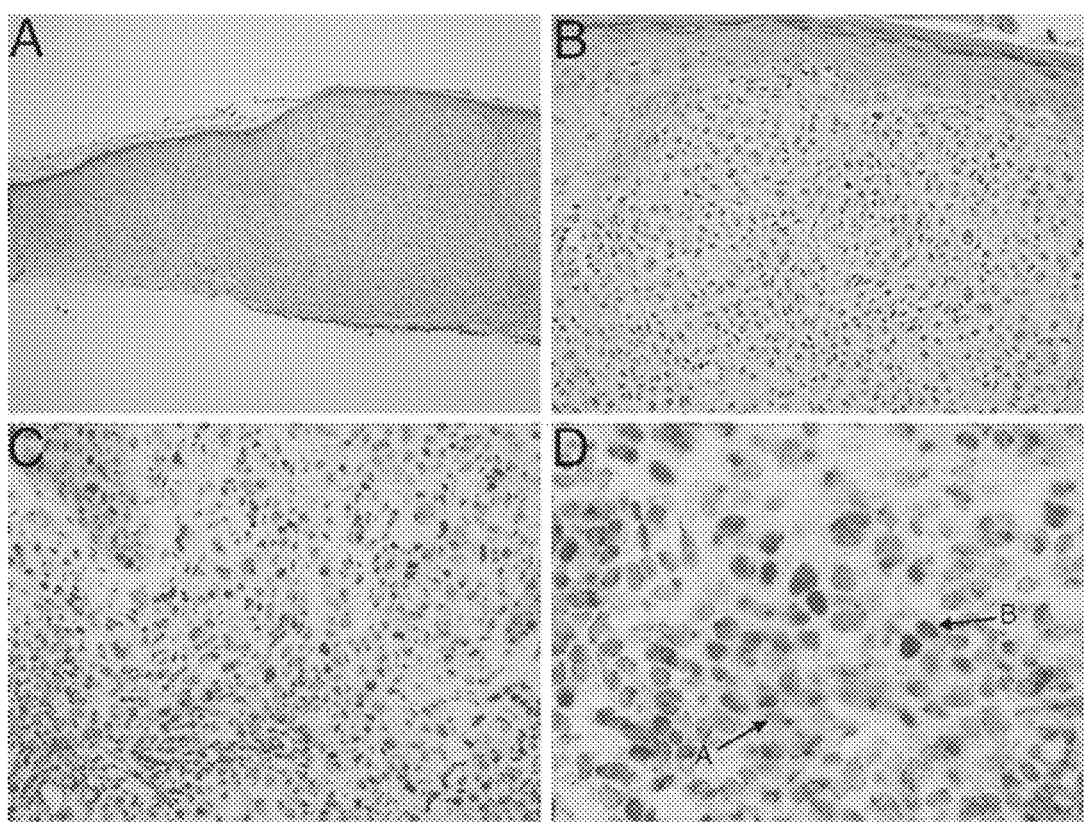
FIG. 14 is a photograph depicting a sAC staining pattern of a superficial spreading melanoma arising within a nevus. (A-B) The low-power view shows a compound melanocytic proliferation with an asymmetrical intraepidermal melanocytic proliferation extending beyond the dermal based component. The dermal component is associated with an effacing growth pattern within the dermis. (C-D) The sAC staining pattern demonstrates a focal perinuclear dot-like staining with pan-nuclear staining observed amidst a minor cell component within the dermis. Interestingly, several cells are without any discernible staining. (D) The invasive melanoma component (arrow B) can be distinguished from the residual nevus component (arrow A) by the sAC stain.
Figure 15:
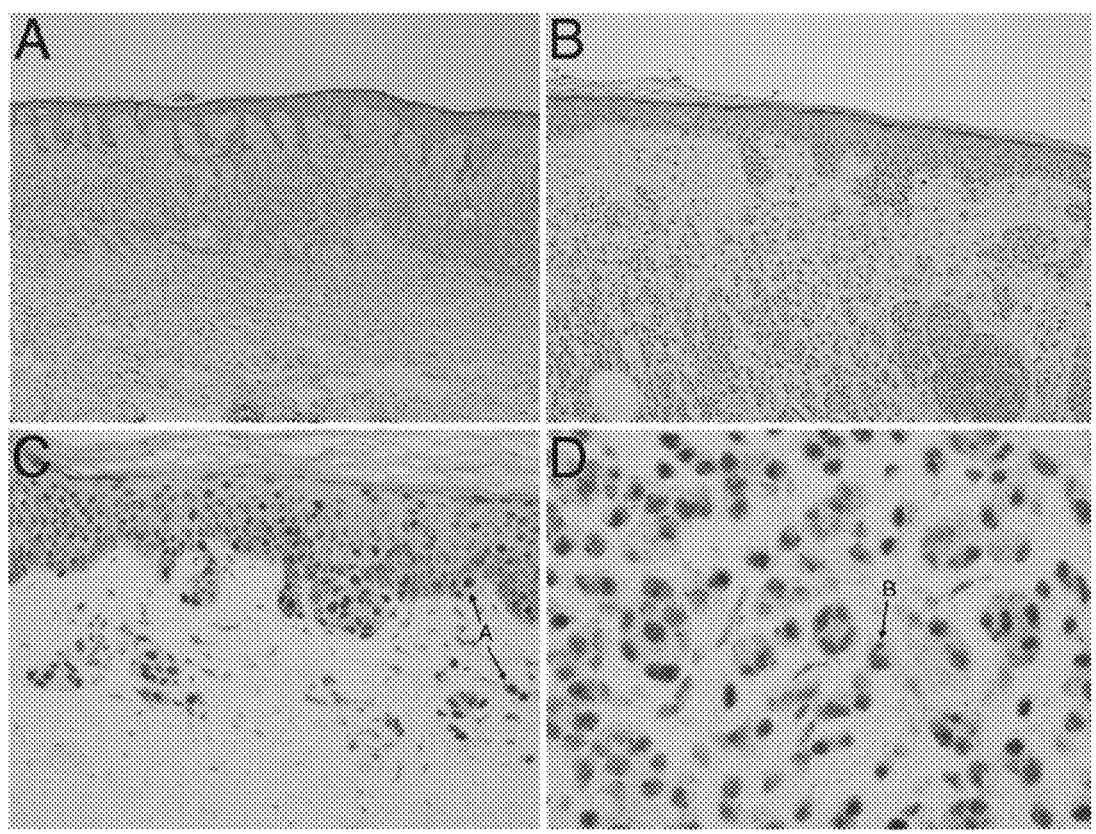
FIG. 15 is a photograph depicting a sAC staining pattern of a superficial spreading melanoma arising within a nevus. (A-B) The excision specimen shows an atypical compound melanocytic proliferation. The intraepidermal component is associated with a high-density, confluent growth pattern along the dermal epidermal junction with foci of pagetoid ascent of severely atypical melanocytes. The intraepidermal component is one of melanoma in situ. There is a dermal component showing variable atypia. (C-D) The sAC staining demonstrates an extensive pan-nuclear staining pattern (arrow A) observed in both atypical singly disposed and nested melanocytes located in the epidermis corresponding to melanoma in situ. Similar staining is noted amidst the melanocytes in the superficial dermis. This component was histologically held to represent invasive melanoma. Interestingly, the dominant component within the dermis which was held to be atypical, although not diagnostic of melanoma, demonstrated a nearly ubiquitous perinuclear dot-like Golgi pattern (arrow B).
Figure 16:
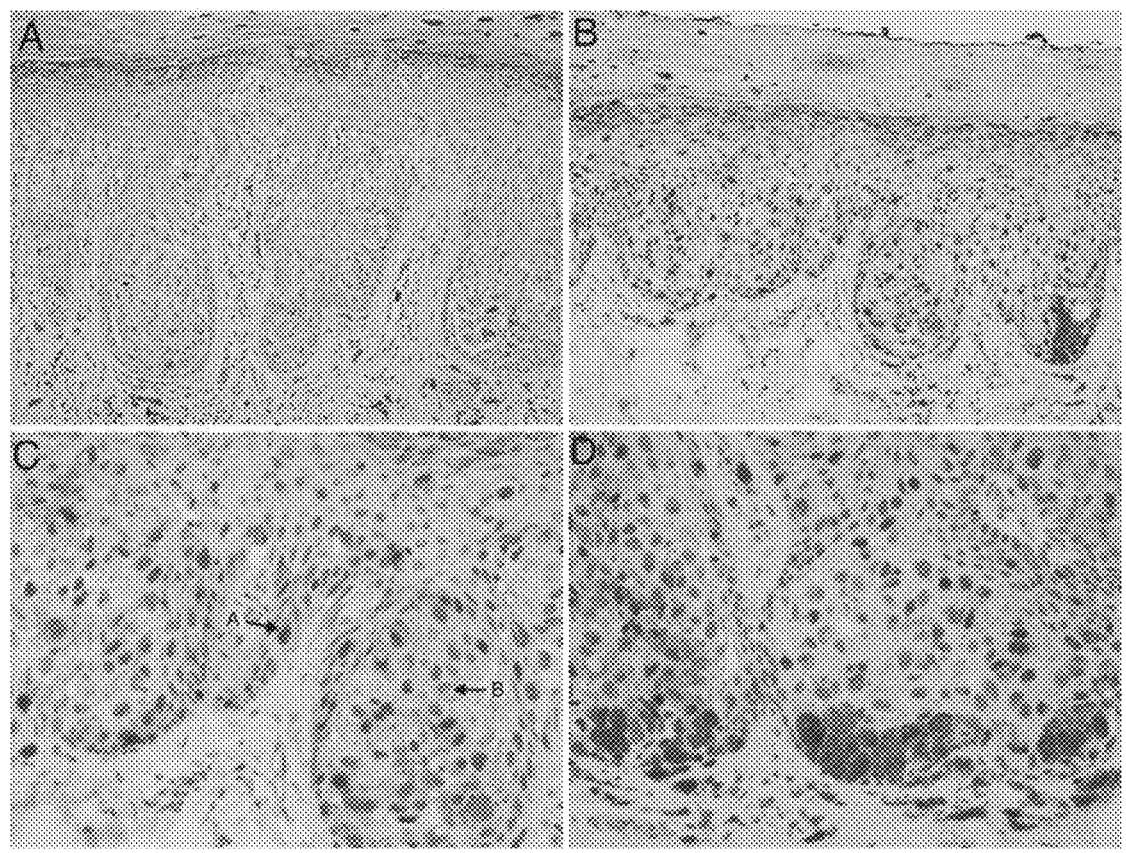
FIG. 16 is a photograph depicting a sAC staining pattern of a superficial spreading melanoma arising in an acral location. (A) The biopsy shows a high-density pagetoid growth of severely atypical epithelioid melanocytes exhibiting a pagetoid growth pattern in the epidermis. Atypical cells extend into the granular cell layer. (B-D) The sAC staining pattern demonstrates a large number of pan-nuclear staining melanocytes (arrow A), few perinuclear dot-like Golgi staining cells (arrow B), and extensive diffuse cytoplasmic staining.

Any discernible lateral invasion within the epidermis beyond the confines of the dermal component defines superficial spreading malignant melanoma. Alternatively, any superficial invasive radial growth phase component with lateral spread beyond the confines of a more deeply invasive component defines superficial spreading malignant melanoma.

sAC staining patterns: Supervening pan-nuclear staining affecting at least 25%, of the cell populace in both the epidermis and dermis is the feature that discriminates superficial spreading melanomas from dysplastic nevi (FIGS. 12-16). In fact, a significant degree of pan-nuclear staining amidst cells in the dermis, as opposed to intraepidermal staining, is an important finding signifying invasive melanoma. In cases arising in pre-existing nevi, the sAC staining pattern can be used to discriminate invasive melanoma cells from residual nevus cells (FIG. 14), the latter having classic perinuclear dot-like Golgi staining (FIG. 14, arrow A) without pan-nuclear staining, versus the invasive melanoma component having a pan-nuclear staining pattern (FIG. 14, arrow B). This discriminant pattern helps to determine the depth of invasion. Pan-nuclear staining clearly defines the in situ and superficially invasive components of the melanoma (FIG. 15, arrow A), while in routine stains, nuclear atypia of the precursor component prohibits this distinction. There is a clear difference between the pan-nuclear staining of melanoma cells versus the dot-like Golgi staining of benign melanocytes (FIG. 15, arrow B). Most cases of superficial spreading melanoma show broad Golgi staining, but some cases show preservation of dot-like Golgi staining, and some cases show no discernible Golgi staining.

Figure 13:
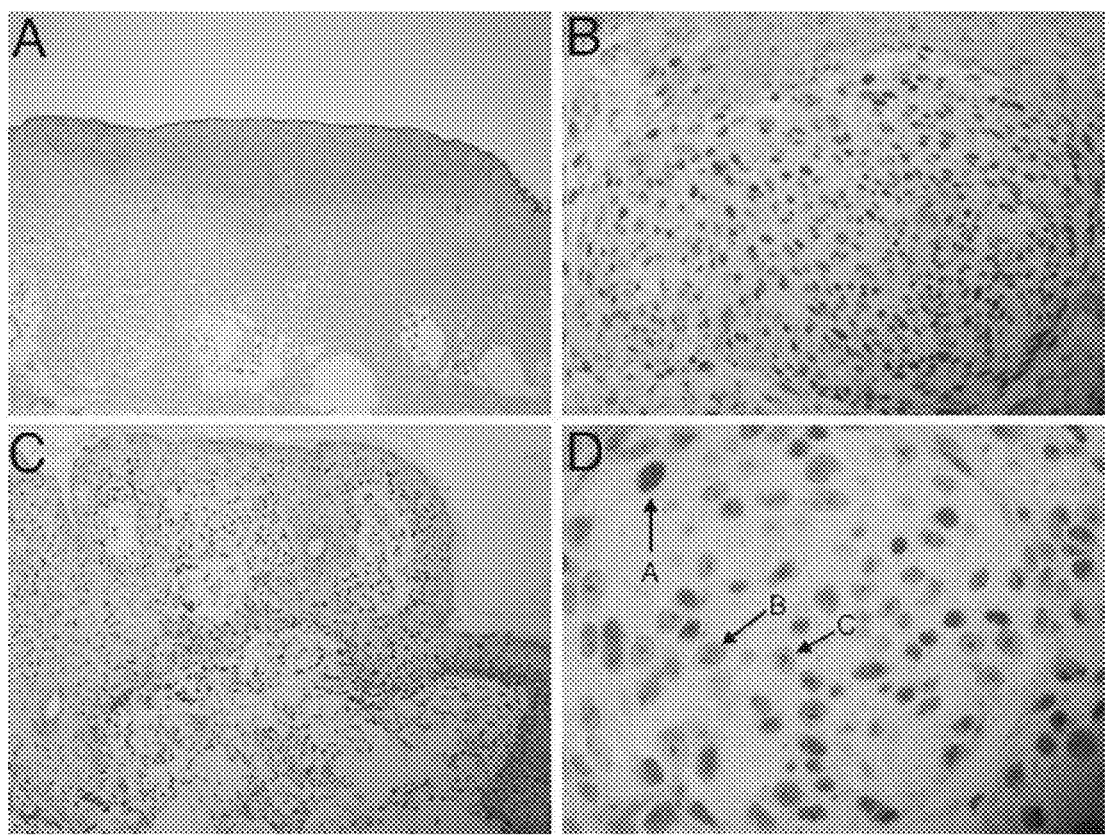
FIG. 13 is a photograph depicting a sAC staining pattern of a superficial spreading melanoma. (A) The low-power view shows a compound melanocytic proliferation with an asymmetrical intraepidermal melanocytic proliferation extending beyond the dermal based component. The dermal component is associated with an effacing growth pattern within the dermis. (B-D) The sAC staining pattern demonstrates a fairly extensive pan-nuclear staining within the epidermis. There is also focal pan-nuclear staining amidst neoplastic cells in the dermis (arrow A). Some nuclei are devoid of staining (arrow B). There is conspicuous nucleolar staining (arrow C). A noticeable lack of Golgi staining is apparent.

Superficial spreading melanomas also can show incomplete granular nuclear staining and nucleolar staining (FIG. 13, arrow C) in addition to pan-nuclear staining (FIG. 13, arrow A). In some instances, cells are devoid of all staining (FIG. 13, arrow B). Variable diffuse cytoplasmic staining also can be present.

The sAC staining pattern in superficial spreading melanoma is constant regardless of anatomic location. Acral melanoma of superficial spreading type demonstrate pan-nuclear (FIG. 16, arrow A), dot-like Golgi (FIG. 16, arrow B), and diffuse cytoplasmic staining and bear no resemblance to acral lentiginous melanomas that show intense pan-nuclear, but little cytoplasmic, expression (FIGS. 9-10).

Nodular Melanoma

Figure 17:
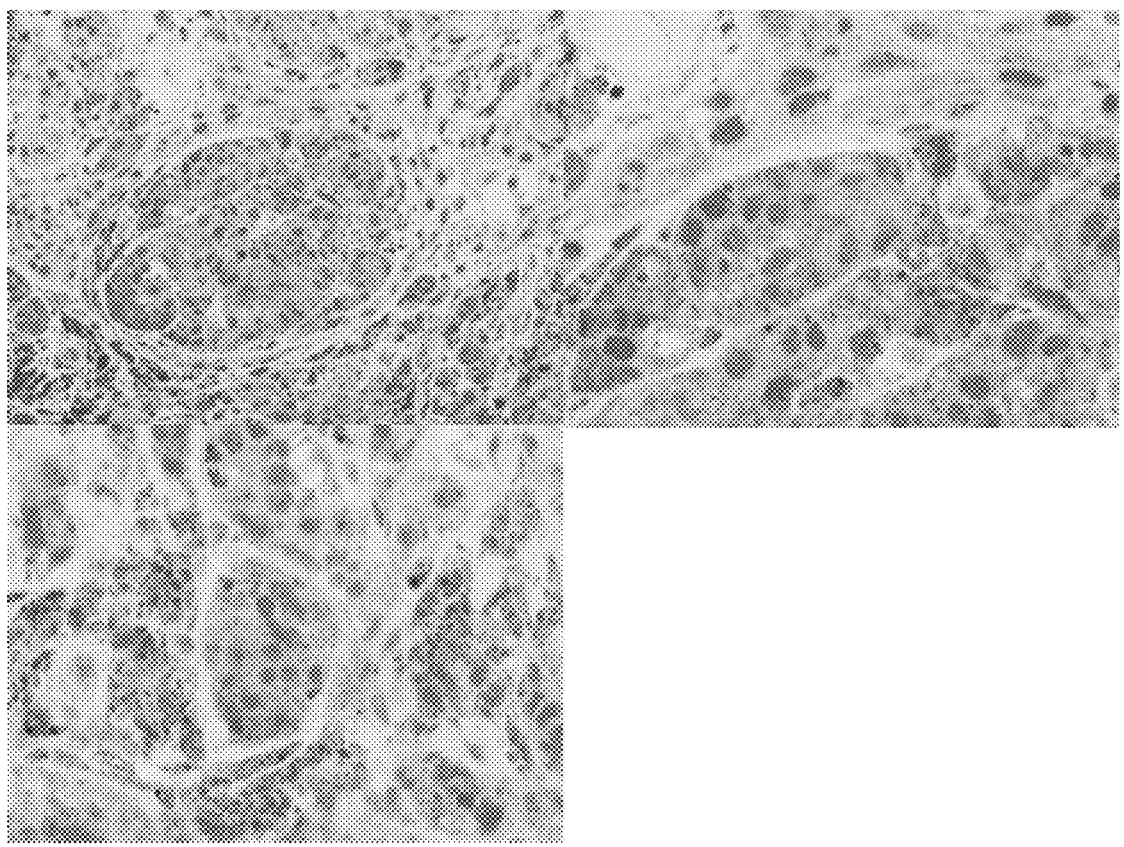
FIG. 17 is a photograph depicting a sAC staining pattern of a nodular melanoma. All three panels show striking pan nuclear staining. Only a minority of cells show any Golgi staining. There is diffuse intense cytoplasmic staining.
Figure 18:
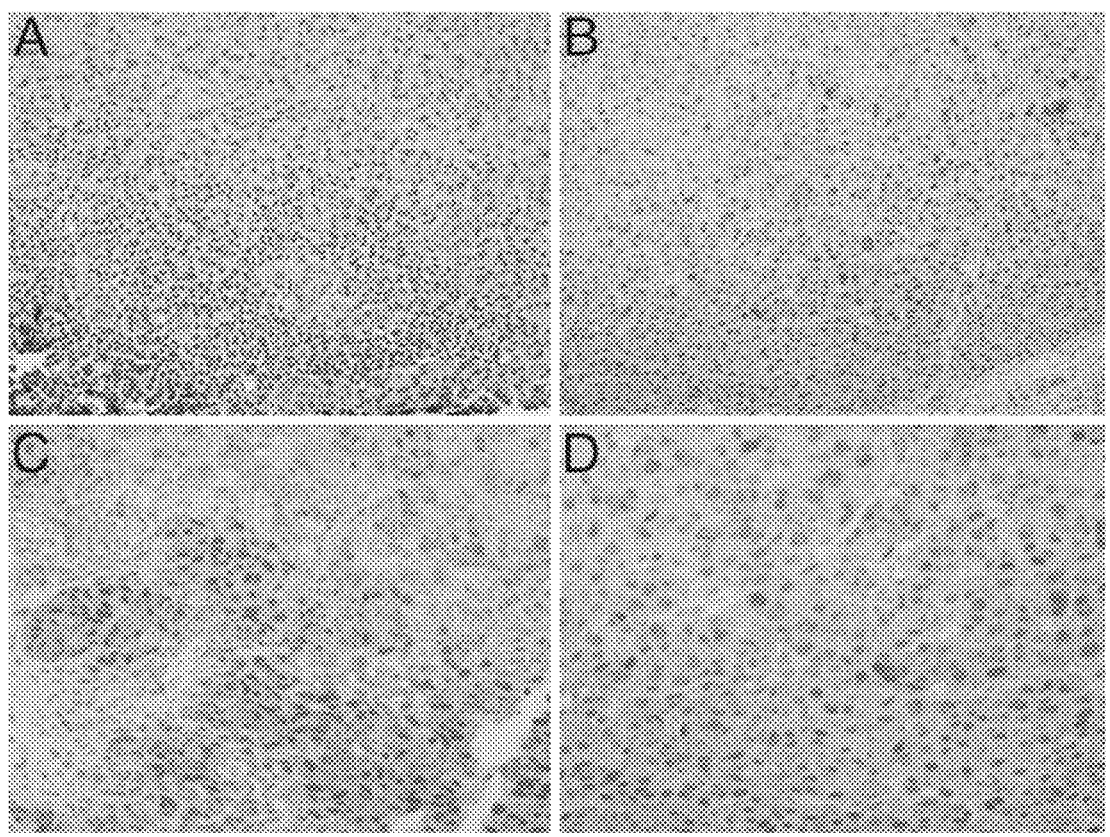
FIG. 18 is a photograph depicting a sAC staining pattern of a nodular melanoma. (A) This is a classic nodular melanoma, showing malignant epithelioid melanocytes with admixed lymphocytes. (B-D) The sAC staining pattern shows diffuse cytoplasmic staining along with focal nuclear staining. The Golgi pattern is not discernible.

Histologic features: Nodular melanomas are characterized by a melanoma exhibiting a pure vertical growth phase without any evidence of a radial growth phase.

sAC staining patterns: Nodular melanomas show pan-nuclear staining, but in fewer cells that in the other melanoma subtypes. Many of the cells also show a prominent nucleolar staining pattern. The dot-like Golgi staining pattern is typically lost, and cytoplasmic staining is primarily diffuse and relatively intense. The classic sAC staining profile of nodular melanoma comprises pan-nuclear staining in nuclei at all levels, cells exhibiting a clustered pattern with nucleolar staining, and diffuse cytoplasmic staining, typically unaccompanied by dot-like Golgi staining. The lesional melanocytes, which do not exhibit pan-nuclear staining, show prominent nucleolar and incomplete granular nuclear staining (FIGS. 17-18).

Metastatic Melanoma

Figure 27:
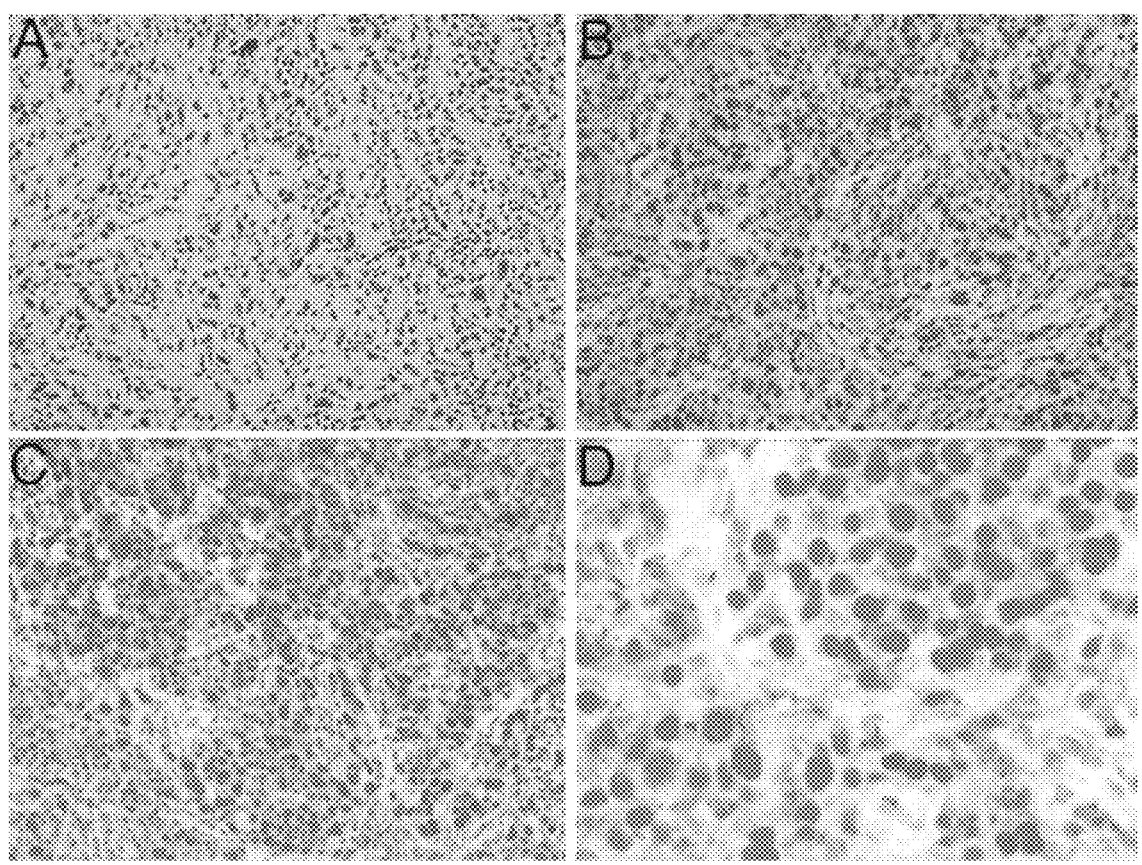
FIG. 27 is a photograph depicting a sAC staining pattern of a metastatic melanoma from the lung. (A) The biopsy shows a poorly differentiated spindle cell tumor. The tumor was S100 positive. There was a prior history of a deeply invasive acral lentignous melanoma. (B-D) sAC staining exhibited extensive pan-nuclear staining without cytoplasmic staining.
Figure 28:
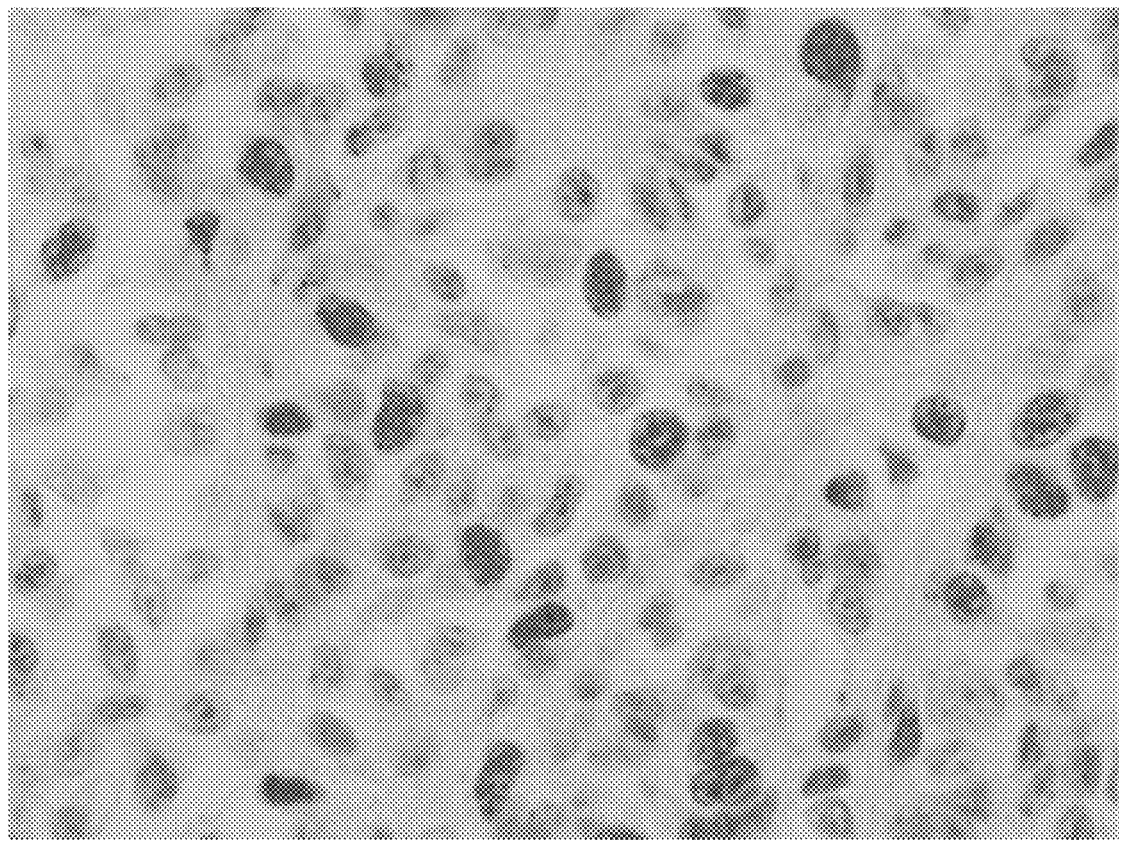
FIG. 28 is a photograph depicting a sAC staining pattern of a metastatic melanoma from the lung. sAC staining demonstrates focal nuclear staining. There is no discernible cytoplasmic staining and Golgi staining is not apparent.

Histologic features: Metastatic melanoma typically manifests as melanoma within the dermis without continuity within the epidermis. It is most characteristically seen in a setting of a patient that has a past history of malignant melanoma where the clinical suspicion is metastatic melanoma. In cases where this histology is present but there is no known history of melanoma, an alternative designation is one of malignant melanoma type unclassified.

sAC staining patterns: In metastatic melanomas with a spindled cytomorphology, the majority of the cells exhibit prominent pan-nuclear staining (FIG. 27). In metastatic melanomas with a high-grade epithelioid appearance, pan-nuclear staining is noted, but is present in a minor cell population (FIG. 28). There is a complete absence of Golgi staining in some cases. In cases where Golgi staining is observed, only a minority of the cell population shows staining and the pattern is very broad, as opposed to the sharp dot-like Golgi staining pattern of a benign or dysplastic nevus. Intense diffuse cytoplasmic staining is very characteristic of metastatic melanoma and is observed in most cases. Nucleolar staining is generally not observed.

When comparing the sAC staining pattern of metastatic deposits to that of benign capsular nevi, the differences are clear, as the metastatic deposits have an abnormal pattern typical of melanoma, while the capsular nevus cells either do not decorate or have reproducible dot-like Golgi staining. The biologic basis for the loss of Golgi and nucleolar staining in metastatic melanoma is unclear, but nonetheless appears to be a hallmark of metastatic melanoma.

The most important indicators of progression from benignancy to malignancy appear to be the loss of dot-like Golgi staining and/or the gain of pan-nuclear staining. A sAC staining pattern comprising dot-like Golgi staining in more than 25% of lesional melanocytes and/or pan-nuclear staining in 0-25% of lesional melanocytes is indicative of a diagnosis of benign nevus, benign capsular nevus, atypical nevus of special sites, or dysplastic nevus. A sAC staining pattern comprising dot-like Golgi staining in 0-25% of lesional melanocytes and/or pan-nuclear staining in more than 25% of lesional melanocytes is indicative of a diagnosis of lentigo maligna melanoma, acral lentiginous melanoma, superficial spreading melanoma, nodular melanoma, or metastatic melanoma.

The invention also provides a kit for use in interpreting melanocytic proliferations. Kits suitable for antibody-based diagnostic applications typically include one, two, or all three of the following items: (i) one or more anti-sAC antibodies, (ii) one or more other reagents and materials for discerning and/or amplifying an sAC staining pattern on a sample, and (iii) instructions for using the kit and/or conducting the inventive method. The anti-sAC antibodies are as described herein. The anti-sAC antibodies can be labeled, or, alternatively, the anti-sAC antibodies can be unlabeled, desirably with the components for labeling included in the kit in separate containers or with a secondary, labeled antibody provided in the kit. The other reagents and materials can be any of the reagents and materials as described herein and can be suitably packaged reagents and materials needed for the particular immunoassay protocol, including solid phase matrices, if applicable, and standards.

The following examples further illustrate the invention but, should not be construed as in any way limiting its scope.

EXAMPLE 1

This example demonstrates the staining of a tissue sample with R21 antibody against sAC to provide an sAC staining pattern. All steps were performed using the Leica Microsystems BOND-MAX™ autostainer (Bannockburn, Ill.).

Dewaxing: Formalin-fixed, paraffin embedded samples of lesional melanocytes were baked at 60° C. for 30 minutes. Slides were then treated with a Leica Microsystems BOND DEWAX SOLUTION™ (AR9222) for 3 minutes at 72° C., followed by washes in BOND DEWAX SOLUTION™ first at 72° C. and then at ambient temperature. Finally, slides were washed three times with ethyl alcohol 200-proof (Pharmco-Aaper, Brookfield, Conn., 111000200) and three times with Leica Microsystems BOND WASH SOLUTION™ (AR9590).

Pre-treatment and blocking: Following the dewaxing procedure, the sections were pre-treated by two washes in Leica Microsystems BOND EPITOPE RETRIEVAL SOLUTION 1™ (AR9961), followed by BOND EPITOPE RETRIEVAL SOLUTION 1™ pre-treatment for 30 minutes at 100° C., and then BOND EPITOPE RETRIEVAL SOLUTION 1™ pre-treatment for 12 minutes at ambient temperature. Before immunostaining, the sections were blocked using the Dako DUAL ENDOGENEOUS ENZYME BLOCK™ (S2003) for 5 minutes, followed by three washes with Leica Microsystems BOND WASH SOLUTION™.

Immunostaining: Leica Microsystems BOND WASH SOLUTION™ was used as the wash buffer in all washing steps described below, unless otherwise noted. The primary antibody (3 mg/ml, 1:9000) was applied for 25 minutes in a buffered Leica Microsystems PRIMARY ANTIBODY DILUENT™ (AR9352). Following this step, the sections were treated by a post primary alkaline phosphatase (AP) step for 20 minutes for signal amplification as part of the procedure detailed in the Leica Microsystems BOND POLYMER AP RED DETECTION™ kit (DS9305). The amplification polymer was then added for 30 minutes, followed by two washes in wash buffer and one wash in deionized water. Finally, the mixed red substrate was applied for 10 minutes, followed by an additional 10 minutes with fresh mixed red substrate, three washes in deionized water only, and, finally, mounting with coverslip.

When a blocking peptide was used, the antibody was pre-diluted in Leica Microsystems PRIMARY ANTIBODY DILUENT™ with blocking peptide (100 fold molar excess) and rocked at room temperature overnight. These pre-diluted solutions were used for immunostaining as above.

Co-staining: Hematoxylin co-stain was used to highlight the nuclei. The stain was incubated on the slide for 5 minutes followed by one wash in 70% alcohol, three washes in 100% alcohol, two washes in Fisherbrand CITRASOLV™ (22-143975), and mounting with a coverslip.

EXAMPLE 2

This example demonstrates that the analysis of a sAC staining pattern of a sample of lesional melanocytes from a subject can be used to provide a diagnosis of melanocytic proliferations for the subject.

Samples of lesional melanocytes were obtained from 140 different subjects and subjected to the procedures described in Example 1 to obtain or discern sAC staining patterns. The 140 sAC staining patterns were analyzed and grouped into categories pertaining to different diagnoses of melanocytic proliferations. The results of this analysis provided the following sAC staining pattern characteristics for each of the diagnoses of melanocytic proliferations.

(1) Benign nevus and capsular nevus of lymph nodes
   (a) Dot-like Golgi staining in >50% of lesional melanocytes
   (b) Weak nucleolar and incomplete granular nuclear staining in 50% of lesional melanocytes, on average
   (c) Pan nuclear staining in <10% of lesional melanocytes
(2) Atypical nevus of special sites
   (a) Pan-nuclear staining in the minority of lesional melanocytes (<10%), although increased with progressive atypia in the epidermis only
   (b) No pan-nuclear dermal staining in lesional melanocytes
   (c) Dot-like Golgi staining in lesional melanocytes, as in benign nevi
(3) Dysplastic nevus
   (a) Predominant dot-like Golgi staining in lesional melanocytes (>50%); minor populace of lesional melanocytes exhibits the broad Golgi staining typically seen in higher grade dysplastic nevi
   (b) Pan-nuclear staining confined to the epidermis and present in a minority of lesional melanocytes, increasing with progressive atypia (mild <10%, moderate/severe 10-25%; rarely over 25%)
   (c) No significant pan-nuclear staining of lesional melanocytes in the dermis
(4) Low-risk conventional atypical Spitz tumor
   (a) Prominent nucleolar staining of lesional melanocytes
   (b) Broad Golgi staining of lesional melanocytes (5) High-risk conventional atypical Spitz tumor
   (a) Prominent nucleolar staining of lesional melanocytes
   (b) Pan-nuclear staining (minority of lesional melanocytes) in both the epidermis and dermis
   (c) Diffuse cytoplasmic staining of lesional melanocytes
   (d) Broad Golgi staining of lesional melanocytes
(6) Superficial atypical Spitz tumor
   (a) Variable pan-nuclear staining in the epidermis with greater number of staining lesional melanocytes as progressive atypia approaches the extent seen in malignant lesions; minority of lesional melanocytes show pan-nuclear staining in the dermis
   (b) Broad Golgi staining of lesional melanocytes
   (c) Prominent nucleolar staining of lesional melanocytes
(7) Low-risk borderline deep penetrating nevus-like lesion
   (a) Dot-like and broad Golgi staining of lesional melanocytes
   (b) Nucleolar and incomplete granular nuclear staining in the majority of lesional melanocytes
   (c) pan-nuclear staining in a minority of lesional melanocytes
   (d) No accentuation in cytoplasmic staining of lesional melanocytes
(8) High-risk borderline deep penetrating nevus-like lesion
   (a) Greater degree of pan-nuclear staining of lesional melanocytes than in low-risk borderline deep penetrating nevus-like lesions
   (b) Diffuse cytoplasmic staining of lesional melanocytes
   (c) Variable Golgi staining of lesional melanocytes, from absent to broad
(9) Dermal variant nevoid borderline tumor
   (a) Dot-like (dominant) Golgi staining lesional melanocytes
   (b) Minor pattern of broad Golgi staining of lesional melanocytes
   (c) Pan-nuclear staining (minority of lesional melanocytes)
(10) Severely atypical nevoid borderline tumor exhibiting borderline features with melanoma of superficial spreading type
   (a) Extensive pan-nuclear staining amidst lesional melanocytes within the epidermis along with broad Golgi staining; a lesser degree of pan-nuclear staining observed amidst lesional melanocytes in the dermis
(11) Lentigo maligna melanoma
   (a) Pan-nuclear staining without Golgi staining of lesional melanocytes
   (b) No discernible diffuse cytoplasmic staining of lesional melanocytes
(12) Acral lentiginous melanoma
   (a) Pan-nuclear staining of lesional melanocytes
   (b) Broad Golgi staining of lesional melanocytes
   (c) No discernible diffuse cytoplasmic staining
(13) Superficial spreading melanoma
   (a) Staining of lesional melanocytes is always nuclear, ranging from nucleolar/incomplete granular nucleolar to pan-nuclear (>25% and usually 50-75%)
   (b) Variable diffuse cytoplasmic staining of lesional melanocytes
   (c) Variable Golgi staining of lesional melanocytes ranging from dot-like (on average <25%) to broad (majority of cases will show some component if not a dominant pattern of broad staining)
(14) Nodular melanoma
   (a) Pan-nuclear staining of lesional melanocytes, although less than other subtypes of melanoma
   (b) Diffuse cytoplasmic staining of lesional melanocytes
   (c) Nucleolar staining of lesional melanocytes
   (d) Absence of perinuclear dot-like Golgi staining of lesional melanocytes
(15) Metastatic melanoma
   (a) Intense diffuse cytoplasmic staining or complete loss of cytoplasmic staining of lesional melanocytes
   (b) No nucleolar staining of lesional melanocytes
   (c) No Golgi staining of lesional melanocytes
   (d) Variable intense pan-nuclear staining of lesional melanocytes

EXAMPLE 3

This example compares the dot-like Golgi and pan-nuclear staining patterns in dysplastic nevi to the dot-like Golgi and pan-nuclear staining patterns in melanoma.

Loss of dot-like Golgi staining with gain of pan-nuclear staining appears to be indicative of melanoma. In the following table (Table 1), loss of dot-like Golgi staining (DG) is assumed when <25% of total melanocytes have this staining pattern (range for nevi 50-75%; range for melanomas 0-25%). Gain of pan-nuclear staining (PN) is assumed when >25% total melanocytes have this staining pattern (range for nevi 0-25%; range for melanomas 50-90%). Melanomas were compared to a combined group of all moderately and severely dyspalstic nevi, with "all melanomas" representing superficial spreading, acral lentiginous, nodular, and lentigo maligna melanomas, and "SSM" representing superficial spreading melanomas.

To determine if particular staining patterns were present or absent in a given type of lesion more often than simple chance, a binomial proportion test was performed (50% assumption being simple chance) with a two-sided student t-test. To determine if there was a qualitative difference in staining pattern between diagnoses, a rank order analysis followed by a Chi Square was performed. To determine if there was a quantitative difference in staining pattern between diagnoses, an NPAIR1WAY with a Mantel-Haenszel Chi-Square was performed, and trends were confirmed with a Spearman Correlation Coefficient analysis.

Sensitivity and specificity were determined for the diagnosis of melanoma with melanoma being compared to moderate/severe dysplastic nevi. Sensitivity was determined by calculating the number of melanoma diagnoses with ≤25% of cells having dot-like Golgi staining and/or >25% of cells having pan-nuclear staining, divided by the total number of melanomas examined. Specificity was determined by calculating the number of moderate/severe dysplastic nevi diagnoses with ≤25% of cells having dot-like Golgi staining and/or >25% of cells having pan-nuclear staining, divided by the total number of moderate/severe dysplastic nevi examined.

| Patterns/Diagnosis | Sensitivity | Specificity |
| --- | --- | --- |
| DG and PN/all melanoma | 98% ($p < 1.2E-10$) (81) | 68% |
| DG or PN/all melanoma | 81% ($p < 1.3E-8$) (81) | 94% |
| PN/all melanoma | 91% ($p < 3.6E-13$) (80) | 92% |
| Dot-golgi/all melanoma | 84% ($p < 1.2E-5$) (81) | 65% |
| DG and PN/SSM | 94% ($p < 2.5E-6$) (53) | 75% |
| DG or PN/SSM | 68% ($p < 2.2E-6$) (53) | 100% |
| PN/SSM | 83% ($p < 3E-10$) (52) | 100% |
| DG/SSM | 68% ($p < 0.006$) (53) | 71% |

The absence of dot-like Golgi staining combined with the presence of pan-nuclear staining was 98% sensitive and 68% specific for the diagnosis of melanoma ($p=1.2E-10$, $n=81$). The presence of pan-nuclear staining was 91% sensitive and 92% specific ($p=3.6E-13$, $n=80$) for the diagnosis of melanoma.

One of the most difficult tasks of a pathologist is the distinction between early superficial spreading melanoma and moderately and severely dysplastic nevi. The combined absence of dot-like Golgi staining with the presence of pan-nuclear staining was 94% sensitive and 75% specific for the diagnosis of superficial spreading melanoma (p=2.5E-6, n=53), over that of moderately and severely dysplastic nevi, and, if only the presence of pan-nuclear staining was considered, the sensitivity was 83% and the specificity was 100% (p=3E-10, n=52).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for diagnosing a melanocytic proliferation in a subject comprising:
   (a) obtaining a sample of lesional melanocytes from a subject,
   (b) staining the sample with a monoclonal antibody that binds specifically to soluble adenylyl cyclase (sAC) to establish a sAC staining pattern, wherein the monoclonal antibody is the R21 monoclonal antibody, the R41 monoclonal antibody, or the R52 monoclonal antibody,
   (c) interpreting the sAC staining pattern, and
   (d) diagnosing a melanocytic proliferation in the subject that is associated with the sAC staining pattern.

2. The method of claim 1, wherein the sAC staining pattern comprises one or more staining patterns selected from the group consisting of:
   (a) perinuclear Golgi staining,
   (b) diffuse cytoplasmic staining,
   (c) nucleolar staining, and
   (d) pan-nuclear staining.

3. The method of claim 2, wherein the sAC staining pattern is indicative of a diagnosis selected from the group consisting of benign nevus, dysplastic nevus, conventional atypical Spitz tumor, superficial atypical Spitz tumor, lentigo maligna melanoma, acral lentiginous melanoma, superficial spreading melanoma, nodular melanoma, and metastatic melanoma.

4. The method of claim 3, wherein the sAC staining pattern comprises:

(a) perinuclear Golgi staining in more than 25% of lesional melanocytes and/or
(b) pan-nuclear staining in 0-25% of lesional melanocytes, which sAC staining pattern is indicative of a diagnosis of benign nevus or dysplastic nevus.

5. The method of claim 3, wherein the sAC staining pattern comprises:
(a) perinuclear Golgi staining in 0-25% of lesional melanocytes and/or
(b) pan-nuclear staining in more than 25% of lesional melanocytes, which sAC staining pattern is indicative of a diagnosis of lentigo maligna melanoma, acral lentiginous melanoma, superficial spreading melanoma, nodular melanoma, or metastatic melanoma.

6. The method of claim 2, wherein the sAC staining pattern distinguishes between a benign neoplasm and a malignant neoplasm.

7. The method of claim 2, wherein the sAC staining pattern distinguishes between a dysplastic nevus and a superficial spreading melanoma.

8. The method of claim 2, wherein the sAC staining pattern distinguishes between a superficial atypical Spitz tumor and a superficial spreading melanoma.

9. The method of claim 2, wherein the sAC staining pattern distinguishes between a benign nevus and a metastatic melanoma.

10. The method of claim 1, wherein the subject is a human.

11. The method of claim 1, wherein the method is used in conjunction with conventional histologic examination of the sample.

* * * * *